(12) United States Patent
Bartos

(10) Patent No.: US 7,935,844 B2
(45) Date of Patent: May 3, 2011

(54) RECOVERY OF ENERGY DURING THE PRODUCTION OF AROMATIC CARBOXYLIC ACIDS

(75) Inventor: Thomas M. Bartos, Naperville, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 11/817,262

(22) PCT Filed: Mar. 20, 2006

(86) PCT No.: PCT/US2006/009828
§ 371 (c)(1),
(2), (4) Date: Aug. 28, 2007

(87) PCT Pub. No.: WO2006/102137
PCT Pub. Date: Sep. 28, 2006

(65) Prior Publication Data
US 2008/0194865 A1    Aug. 14, 2008

Related U.S. Application Data

(60) Provisional application No. 60/663,792, filed on Mar. 21, 2005.

(51) Int. Cl.
*C07C 51/16* (2006.01)
(52) U.S. Cl. ........................................ 562/409; 562/408
(58) Field of Classification Search .......................... None
See application file for complete search history.

(56) References Cited

U.S. PATENT DOCUMENTS

| | | | |
|---|---|---|---|
| 2,833,816 | A | 5/1958 | Saffer |
| 3,584,039 | A | 6/1971 | Meyer |
| 4,626,598 | A | 12/1986 | Packer et al. |
| 4,629,715 | A | 12/1986 | Schroeder |
| 4,782,181 | A | 11/1988 | James |
| 4,892,972 | A | 1/1990 | Schroeder et al. |
| 5,081,290 | A | 1/1992 | Partenheimer et al. |
| 5,103,933 | A | 4/1992 | Huff |
| 5,112,992 | A | 5/1992 | Belmonte et al. |
| 5,175,355 | A | 12/1992 | Streich et al. |
| 5,198,156 | A | 3/1993 | Middleton et al. |
| 5,200,557 | A | 4/1993 | Gee et al. |
| 5,304,676 | A | 4/1994 | Hindmarsh et al. |
| 5,354,898 | A | 10/1994 | Schroeder |
| 5,362,908 | A | 11/1994 | Schroeder et al. |

(Continued)

FOREIGN PATENT DOCUMENTS

EP        0 498 591        8/1992

(Continued)

*Primary Examiner* — Karl J Puttlitz
(74) *Attorney, Agent, or Firm* — Stephen L. Hensley

(57) ABSTRACT

Energy is recovered during the production of aromatic carboxylic acids by liquid phase oxidation of aromatic hydrocarbons by performing a high efficiency separation on the reactor overhead vapor to form a high pressure gaseous overhead stream comprising water and organic impurities; recovering heat energy from the high pressure gaseous overhead stream by exchanging heat with a suitable heat sink material such that a condensate comprising from about 20 wt % to about 60 wt % of the water present in the high pressure gaseous overhead stream is formed and a high pressure off-gas is formed; and recovering energy in the form of work from the high pressure off-gas. Preferably such work is recovered using isentropic means for energy recovery, for example an expander. Apparatus for such process is also provided.

20 Claims, 3 Drawing Sheets

U.S. PATENT DOCUMENTS

| | | | |
|---|---|---|---|
| 5,612,007 A | | 3/1997 | Abrams |
| 5,616,792 A | | 4/1997 | Bartos et al. |
| 5,679,846 A | | 10/1997 | Hindmarsh et al. |
| 5,723,656 A | * | 3/1998 | Abrams ........................ 562/412 |
| 5,904,423 A | | 5/1999 | Forschner et al. |
| 6,137,001 A | * | 10/2000 | Broeker et al. ............... 562/413 |
| 6,143,925 A | | 11/2000 | Tomitaka et al. |
| 6,194,607 B1 | | 2/2001 | Jhung et al. |
| 6,504,051 B1 | | 1/2003 | Miller, Jr. et al. |
| 6,852,879 B2 | | 2/2005 | Belmonte et al. |
| 7,135,596 B2 | | 11/2006 | Nubel et al. |
| 2005/0010066 A1 | * | 1/2005 | Lin ............................... 562/414 |

FOREIGN PATENT DOCUMENTS

| | | |
|---|---|---|
| GB | 1373230 | 11/1974 |
| WO | WO 96/11899 | 4/1996 |
| WO | WO 97/27168 | 7/1997 |

* cited by examiner

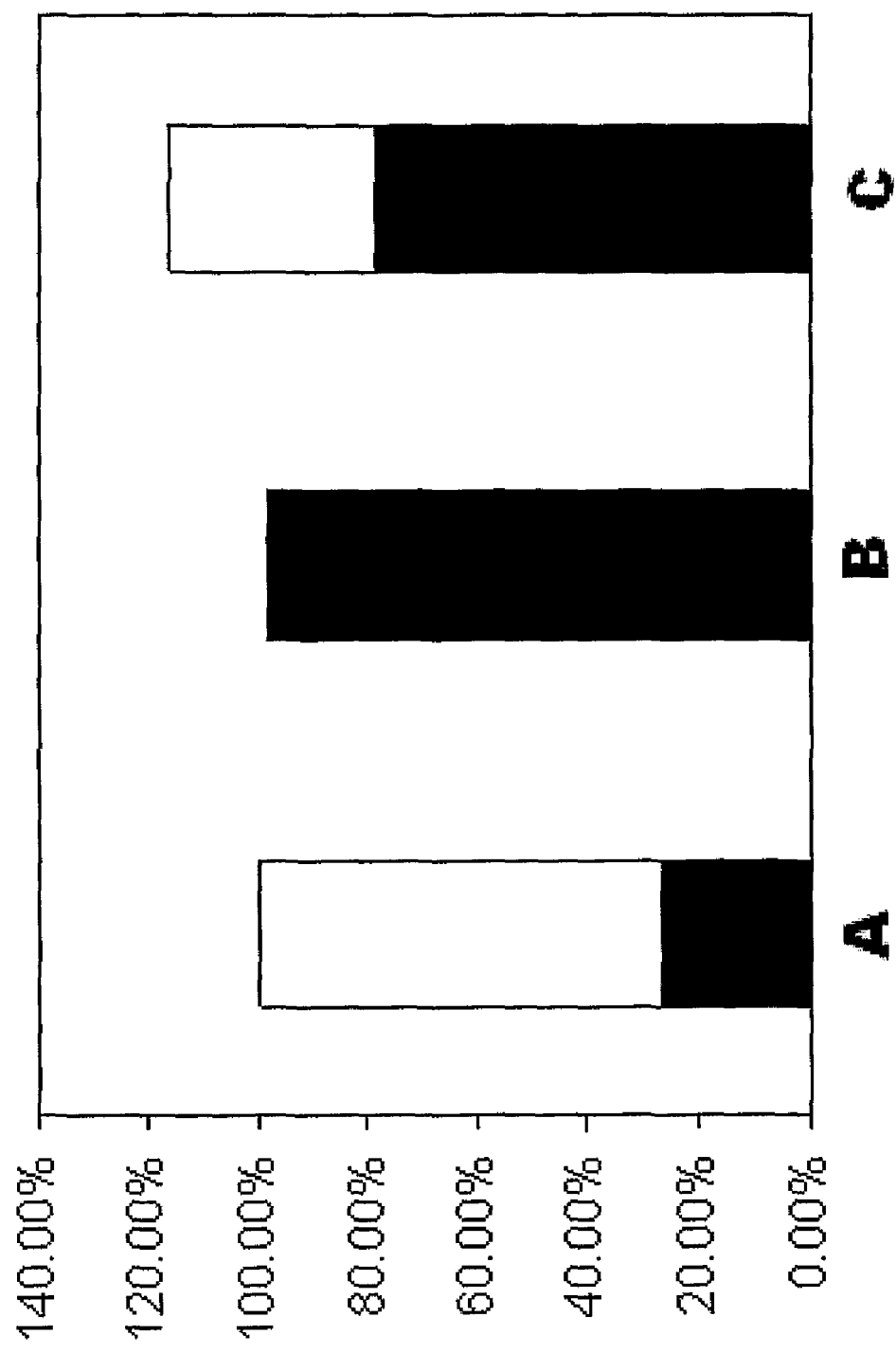

RECOVERY OF ENERGY DURING THE PRODUCTION OF AROMATIC CARBOXYLIC ACIDS

BACKGROUND OF THE INVENTION

Aromatic carboxylic acids such as benzoic, phthalic, terephthalic, isophthalic, trimellitic, pyromellitic, trimesic and naphthalene dicarboxylic acids are important intermediates for many chemical and polymer products. Aromatic carboxylic acids can be produced by liquid phase oxidation of an appropriate aromatic hydrocarbon feedstock. For example, U.S. Pat. No. 2,833,816, hereby incorporated by reference, discloses the liquid phase oxidation of xylene isomers into corresponding benzene dicarboxylic acids in the presence of bromine using a catalyst having cobalt and manganese components. As further example, U.S. Pat. No. 5,103,933, incorporated by reference herein, discloses that liquid phase oxidation of dimethylnaphthalenes to naphthalene dicarboxylic acids can also be accomplished in the presence of bromine and a catalyst having cobalt and manganese components. Typically, aromatic carboxylic acids are purified in a subsequent process involving contacting crude aromatic carboxylic acid with a catalyst and hydrogen in a reducing environment as described, for example, in U.S. Pat. No. 3,584,039, U.S. Pat. No. 4,892,972, and U.S. Pat. No. 5,362,908.

Liquid phase oxidation of aromatic hydrocarbons to aromatic carboxylic acid is conducted using a reaction mixture comprising aromatic hydrocarbons and a solvent. Typically, the solvent comprises a $C_1$-$C_8$ monocarboxylic acid, for example acetic acid or benzoic acid, or mixtures thereof with water. As used herein, "aromatic hydrocarbon" means a molecule composed of carbon atoms and hydrogen atoms, and having one or more aromatic ring, for example a benzene or naphthalene ring. For purposes of this application, "aromatic hydrocarbon" includes such molecules having one or more hetero atoms such as oxygen or nitrogen atoms. Aromatic hydrocarbons suitable for liquid phase oxidation to produce aromatic carboxylic acid generally comprise an aromatic hydrocarbon having at least one substituent group that is oxidizable to a carboxylic acid group for example alkyl aromatic hydrocarbons such as dimethyl benzenes and dimethyl naphthalenes. As used herein, "aromatic carboxylic acid" means an aromatic hydrocarbon with at least one carboxylic acid group.

A catalyst is also present in the oxidation reaction mixture. Typically, the catalyst comprises a promoter, for example bromine, and at least one suitable heavy metal component. Suitable heavy metals include heavy metals with atomic weight in the range of about 23 to about 178. Examples include cobalt, manganese, vanadium, molybdenum, chromium, iron, nickel, zirconium, cerium or a lanthanide metal such as hafnium. Suitable forms of these metals include for example, acetates, hydroxides, and carbonates.

A source of molecular oxygen is also introduced into the reactor. Typically, oxygen gas is used as a source of molecular oxygen and is bubbled or otherwise mixed into the liquid phase reaction mixture. Air is generally used to supply the oxygen.

Subsequent purification processes typically include contacting a solution of the crude aromatic carboxylic acid product of the oxidation with hydrogen and a catalyst under reducing conditions. The catalyst used for such purification typically comprises one or more active hydrogenation metals such as ruthenium, rhodium, palladium, or platinum, on a suitable support, for example, carbon or titania.

Many modifications and improvements have been made to the liquid-phase oxidation process, for example: U.S. Pat. No. 6,194,607 to Jhung et al. discloses the addition of an alkali metal or alkaline earth metal to the reaction mixture in the oxidation of xylene isomers to benzene dicarboxylic acids; U.S. Pat. No. 5,112,992 to Belmonte et al. discloses the addition of hafnium to oxidation catalysts; U.S. Pat. No. 5,081,290 to Partenheimer et al. discloses manipulation of acetate concentration to control the rate of oxidation.

The oxidation reaction in the liquid phase oxidation of aromatic hydrocarbons is an exothermic reaction. Heat of reaction often is removed by boiling the liquid reaction mixture. A vapor phase is formed above the liquid body within the reaction vessel as a result. Such vapor phase typically contains a significant amount of reaction solvent. Overhead gases commonly are removed from the reaction vessel to control the reaction exotherm but such removal represents a significant solvent loss. Significant solvent loss would be undesirable and recovery of solvent from the vapor phase is advantageous. The removed overhead gases can be at least partially condensed and recycled to the reaction vessel in the form of condensate or used elsewhere in the process, downstream process steps or integrated operations.

The overhead gases removed from the oxidation reaction are typically at high pressure and contain a considerable amount of energy. The recovery of energy from oxidation reaction overhead gas significantly reduces the overall energy demand of the aromatic carboxylic acid production process. The importance of such energy recovery continues to grow as global energy demand grows and as demand for particular aromatic carboxylic acids grows. Increasing environmental and regulatory constraints on many energy production methods further raise the importance of recovering process energy.

Efforts have been made to recover energy from the high pressure overhead gases by condensing such stream and exchanging the recovered heat to produce moderate pressure steam. In such condensing operations, all or substantially all of the water in the gaseous stream entering the condenser is condensed to liquid form. U.S. Pat. Nos. 5,723,656 and 5,612,007 to Abrams, incorporated by reference herein, disclose, in part, a liquid phase oxidation process wherein oxidation overhead gas is directed to a high pressure, high efficiency separation apparatus to remove at least 95 wt. % of the solvent from the oxidation overhead gas and forming a high pressure overhead gaseous stream which is directed to a means for energy recovery.

U.S. Pat. No. 6,504,051 to Miller et al., incorporated by reference herein, discloses, in part, a liquid phase oxidation process with recovery of energy from reactor off-gas as in Abrams wherein oxidation overhead gas is directed to a water removal column from which is obtained an overhead vapor stream comprising oxygen depleted off-gas, water and minor amounts of solvent and reaction byproducts. Miller et al. disclose separating the overhead vapor stream into a first portion which can be directed to an energy recovery device and a second portion which is directed to a condenser from which the condensable components are returned to the water removal column and the remaining gas can be directed to an energy recovery device.

The energy recovery schemes disclosed by Abrams and by Miller et al. can recover a significant portion of the energy available in the high pressure gaseous overhead stream. However, a significant amount of the energy available in the high pressure gaseous overhead stream remains untapped. Past attempts to recover energy by condensing all or a portion of the high pressure gaseous overhead stream have employed complete condensation. Other attempts have relied on expansion of an uncondensed stream or of the non-condensable gas from a completely condensed stream for energy recovery. As energy demand increases overall, demand for certain aromatic carboxylic acid increases, and environmental and regulatory constraints upon energy production methods increase, the importance of recovering at least some portion of such untapped energy also increases.

There is a need, therefore, for an improved process for the recovery of energy from overhead gases produced during the liquid phase oxidation of aromatic hydrocarbons to produce aromatic carboxylic acids.

SUMMARY OF THE INVENTION

We have found that a surprising amount of energy can be recovered from a high pressure gaseous overhead stream formed from reaction overhead vapor during the liquid-phase oxidation of aromatic hydrocarbons to produce aromatic carboxylic acids by recovering heat energy using partial condensation followed by recovering energy in the form of work, preferably using isentropic means for energy recovery, more preferably using an expander. Unlike previous energy recovery methods which extract heat energy by substantially complete condensation, partially condensing the high pressure gaseous overhead stream allows significant recovery of heat energy while still leaving substantial energy in the high pressure off-gas exiting the condenser which can be recovered as work. Energy recovery by the combination of heat extraction and work extraction advantageously employs each energy recovery method at a point where it is well suited.

In one embodiment, this invention is a process for energy recovery during the production of aromatic carboxylic acids by liquid phase oxidation of aromatic hydrocarbons wherein reaction overhead vapor comprising reaction solvent and water is formed. The process comprises the steps of performing a high efficiency separation on the reaction overhead vapor to form a high pressure gaseous overhead stream comprising water and organic impurities; recovering heat energy from the high pressure gaseous overhead stream by exchanging heat with a suitable heat sink material such that a condensate comprising from about 20 wt % to about 60 wt % of the water present in the high pressure gaseous overhead stream is formed and a high pressure off-gas is formed; and recovering energy in the form of work from the high pressure offgas. Optionally, the process can further comprise the step of oxidizing at least a portion of the organic impurities by subjecting the high pressure offgas to thermal oxidation before recovering energy in the form of work from the high pressure offgas. Preferably, such thermal oxidation is catalytic. Preferably, the step of recovering energy in the form of work includes directing at least a portion of the high pressure offgas to an expander. Preferably the step of recovering energy in the form of work from the high pressure offgas is performed using isentropic means for energy recovery, preferably an expander.

In another embodiment, this invention provides a process for the production of aromatic carboxylic acid. The process comprises the steps of oxidizing, in a reaction zone comprising at least one reaction vessel, aromatic hydrocarbon with an oxidant gas to form aromatic carboxylic acid in a reaction solvent comprising a $C_1$-$C_8$ monocarboxylic acid in the presence of a catalyst comprising at least one heavy metal with atomic weight in the range of about 23 to about 178 and a halogen promoter under liquid phase conditions at temperatures in the range from about 120° C. to about 250° C. to form an aromatic carboxylic acid product and a reaction overhead vapor comprising water and solvent vapors; performing a high efficiency separation on the reaction overhead vapor to form a liquid bottoms stream comprising at least 95 wt % of the solvent from the reaction overhead vapor and a high pressure gaseous overhead stream comprising at least 50 wt % of the water from the reaction overhead vapor; recovering energy in the form of heat by exchanging heat from the high pressure gaseous overhead stream with a suitable heat sink material such that a condensate comprising from about 20 wt % to about 60 wt % of the water in the high pressure gaseous overhead stream is formed and a high pressure off-gas is formed; and recovering energy in the form of work from the high pressure off-gas.

Optionally, the process can further comprise the step of returning all or a portion of the liquid bottoms stream to the reaction zone. Preferably, the step of recovering energy in the form of work includes directing at least a portion of the high pressure off-gas to an expander. Preferably, the step of recovering energy in the form of work from the high pressure off-gas is performed using isentropic means for energy recovery, more preferably an expander.

In another embodiment, this invention provides an apparatus for the efficient recovery of energy from reaction overhead vapor formed during the production of aromatic carboxylic acid by liquid phase oxidation of aromatic hydrocarbon. The apparatus comprises a reaction vessel having a vent for removing reaction overhead vapor; a high efficiency separation apparatus in fluid communication with the reaction vessel having at least one vapor inlet for receiving reaction overhead vapor from the reaction vessel, at least one liquid inlet for receiving liquid for countercurrent contact with the reaction overhead vapor, at least one liquid outlet for removing liquid and at least one gas outlet for removing a high pressure gaseous overhead stream; a condenser in fluid communication with the high efficiency separation apparatus, the condenser being adapted to extract energy from the high pressure gaseous overhead stream by partially condensing at least a portion of the high pressure overhead gaseous stream and exchanging heat with a heat sink material; and an expander in fluid communication with the condenser having at least one inlet for receiving off-gas comprising water and at least one outlet for expelling vent gas at lower pressure that the off-gas. The high efficiency separation apparatus can be one or more high efficiency distillation columns. Preferably, the condenser is adapted to condense from about 20 wt % to about 60 wt % of water present in the high pressure overhead gaseous stream. Preferably, the apparatus further comprises a thermal oxidation unit in fluid communication with the condenser and the expander. Optionally, the condenser can be further adapted to return condensed fluid from the condenser to the high efficiency separation apparatus.

DESCRIPTION OF DRAWINGS

FIG. 3 is a chart representing energy recovery conducted according to 2 existing schemes compared with energy recovery in accordance with an embodiment of this invention.

DESCRIPTION OF THE PREFERRED EMBODIMENT(S)

Figure 1:
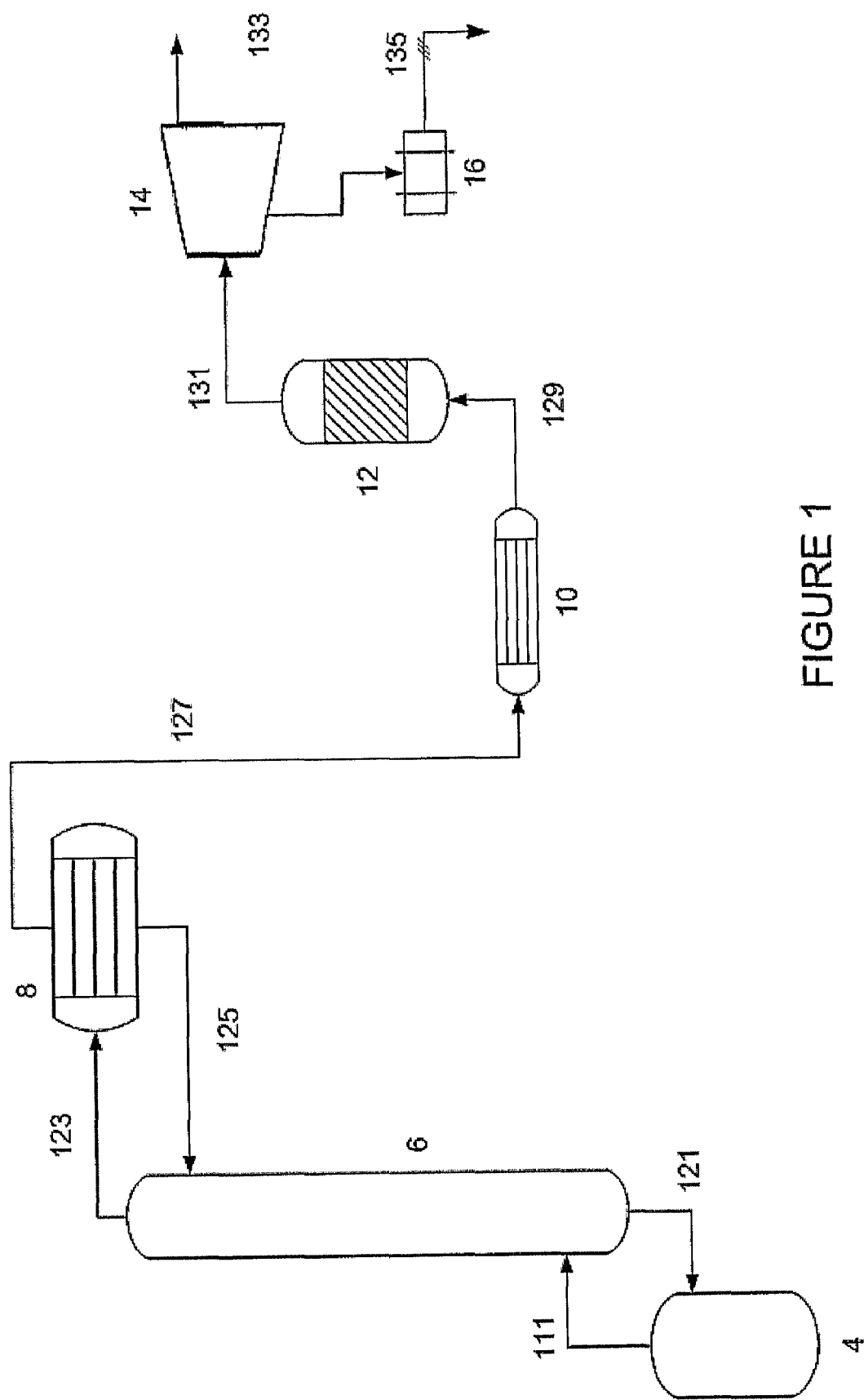
FIG. 1 is a process flow diagram representing an embodiment of this invention.

This invention provides improved processes and apparatuses for recovery of energy from reactor overhead vapor formed during the production of aromatic carboxylic acids by liquid-phase oxidation of aromatic hydrocarbons. Energy is recovered from a high pressure gaseous overhead stream resulting from a high efficiency separation performed on the reactor overhead vapor. Energy is recovered in the form of heat and in the form of work. The combination of the two forms of energy recovery results in a greater total amount of recovered energy.

Water present in such high pressure gaseous overhead stream represents a significant source of energy. We have found that the combination of extracting energy from the water in the form of heat and in the form of work results in a significantly greater total energy recovery than by extracting energy primarily in the form of heat or primarily in the form of work.

Extracting heat energy from the high pressure gaseous overhead stream is most effective when the stream is at its hottest temperature. As the stream is cooled, heat energy extraction becomes less effective than extraction of energy in the form of work. Energy recovery by the combination of heat extraction and work extraction advantageously employs each energy recovery method at a point where it is well suited. Surprisingly, using such a combination, a significantly greater amount of energy can be recovered.

In an embodiment, energy is recovered from such a high pressure gaseous overhead stream as heat by condensing only a portion of the water present and energy is recovered as work by expansion of a stream comprising the uncondensed portion of water.

"Condensation" or "condensing" as used herein, refers to condensation of water in a stream together with other species which condense under like conditions. "Complete condensation" as used herein, means greater than about 90 wt % of the water in a stream is condensed.

Total energy recovery is significantly greater from the combination of extracting heat energy by partial condensation of the high pressure gaseous overhead stream and extracting work from the uncondensed portion of the high pressure gaseous overhead stream than energy recovery from commercial embodiments of either prior art energy recovery from a high pressure gaseous overhead stream comprising water using expansion without condensation or prior art energy recovery using a combination of complete condensation and expansion.

The energy recovery provided by the process and the apparatus of this invention is described in more detail below.

The liquid-phase oxidation of aromatic hydrocarbons to produce aromatic carboxylic acids can be conducted as a batch process, a continuous process, or a semicontinuous process. The oxidation reaction is performed in a reaction zone typically comprising one or more reactors. A reaction mixture is formed by combining components comprising an aromatic hydrocarbon feed, solvent, and catalyst with a promoter, typically bromine. In a continuous or semicontinuous process, the reaction mixture components preferably are combined in a mixing vessel before being introduced into the reaction zone, however, the reaction mixture can be formed in the reaction zone.

Aromatic carboxylic acids for which the invention is suited include mono- and polycarboxylated species having one or more aromatic rings and which can be manufactured by reaction of gaseous and liquid reactants in a liquid phase system. Examples of aromatic carboxylic acids for which the invention is particularly suited include terephthalic acid, trimesic acid, trimellitic acid, phthalic acid, isophthalic acid, benzoic acid and naphthalene dicarboxylic acids.

Suitable aromatic hydrocarbon feed generally comprises an aromatic hydrocarbon having at least one group that is oxidizable to a carboxylic acid group. The oxidizable substituent or substituents can be an alkyl group, such as a methyl, ethyl or isopropyl group. It also can be a group already containing oxygen, such as a hydroxyalkyl, formyl or keto group. The substituents can be the same or different. The aromatic portion of feedstock compounds can be a benzene nucleus or it can be bi- or polycyclic, such as a naphthalene nucleus. The number of oxidizable substituents on the aromatic portion of the feedstock compound can be equal to the number of sites available on the aromatic portion, but is generally fewer than all such sites, preferably 1 to about 4 and more preferably 1 to 3. Examples of useful feed compounds include toluene, ethylbenzene, ortho-xylene, para-xylene, meta-xylene, 1-formyl-4-methylbenzene, 1-hydroxymethyl-4-methylbenzene, 1,2,4-trimethylbenzene, 1-formyl-2,4-dimethylbenzene, 1,2,4,5-tetramethylbenzene, alkyl-, hydroxymethyl-, formyl- and acyl-substituted naphthalene compounds, such as 2,6- and 2,7-dimethylnaphthalenes, 2-acyl-6-methylnaphthalene, 2-formyl-6-methylnaphthalene, 2-methyl-6-ethylnaphthalene and 2,6-diethylnaphthalene, tolualdehydes, alkyl substituted benzenes, alkyl substituted naphthalenes, toluic acids, methylacetophenone, alkyl benzyl alcohols, partially oxidized intermediates of any of the foregoing, and any combination thereof.

For manufacture of aromatic carboxylic acids by oxidation of corresponding aromatic hydrocarbon pre-cursors, e.g., manufacture of terephthalic acid from para-disubstituted benzenes or naphthalene dicarboxylic acids from disubstituted naphthalenes, it is preferred to use relatively pure feed materials, and more preferably, feed materials in which content of the pre-cursor corresponding to the desired acid is at least about 95 wt. %, and more preferably at least 98 wt. % or even higher. A preferred aromatic hydrocarbon feed for use to manufacture terephthalic acid comprises paraxylene. Toluene is a preferred feed material for making benzoic acid.

Solvents comprising an aqueous carboxylic acid, for example benzoic acid, and especially a lower alkyl (e.g., $C_1$-$C_8$) monocarboxylic acid, for example acetic acid, are preferred because they tend to be only sparingly prone to oxidation under typical oxidation reaction conditions used for manufacture of aromatic carboxylic acids, and can enhance catalytic effects in the oxidation. Specific examples of suitable carboxylic acid solvents include acetic acid, propionic acid, butyric acid, benzoic acid and mixtures thereof. Ethanol and other co-solvent materials which oxidize to monocarboxylic acids under typical oxidation reaction conditions also can be used as is or in combination with carboxylic acids with good results. Of course, for purposes of overall process efficiency and minimizing separations, it is preferred that when using a solvent comprising a mixture of monocarboxylic acid and such a co-solvent, the co-solvent should be oxidizable to the monocarboxylic acid with which it is used.

Catalysts used according to the invention comprise materials that are effective to catalyze oxidation of the aromatic hydrocarbon feed to aromatic carboxylic acid. Preferably, the catalyst is soluble in the liquid oxidation reaction mixture to promote contact among catalyst, oxygen and liquid feed; however, heterogeneous catalyst or catalyst components may also be used. Typically, the catalyst comprises a bromine promoter and at least one suitable heavy metal component such as a metal with atomic weight in the range of about 23 to about 178. Examples of suitable heavy metals include cobalt, manganese, vanadium, molybdenum, chromium, iron, nickel, zirconium, cerium or a lanthanide metal such as hafnium. Suitable forms of these metals include for example, acetates, hydroxides, and carbonates. The catalyst preferably comprises cobalt compounds alone or in combination with one or more of manganese compounds, cerium compounds, zirconium compounds, or hafnium compounds.

Typically, a promoter is used to promote oxidation activity of the catalyst metal, preferably without generation of undesirable types or levels of by-products, and is preferably used in a form that is soluble in the liquid reaction mixture. Halogen compounds are commonly used as a promoter, for example hydrogen halides, sodium halides, potassium halides, ammonium halides, halogen-substituted hydrocarbons, halogen-substituted carboxylic acids and other halogenated compounds. Preferably, bromine compounds are used as a promoter. Suitable bromine promoters include bromoanthracenes, $Br_2$, HBr, NaBr, KBr, $NH_4Br$, benzyl-bromide, bromo acetic acid, dibromo acetic acid, tetrabromoethane, ethylene dibromide, bromoacetyl bromide or mixtures thereof.

The oxidation reaction is conducted in a reaction zone typically comprising one or more reactor vessels. Suitable oxidation reactor vessels are those constructed to withstand high pressure and temperature conditions and corrosive liquid and vapor phase contents used and present in the reaction zone, which allow for addition and mixing of catalyst, liquid and gaseous reactants and solvent, removal of aromatic carboxylic acid product or a liquid comprising such product for recovery and removal of high pressure vapor generated by the liquid phase oxidation reaction for controlling the heat of the reaction. Reactor types which can be used include, but are not limited to, continuous stirred tank reactors and plug-flow reactors. Commonly, oxidation reactors comprise a columnar vessel, normally with a central axis which extends vertically when the vessel is positioned for process use, having one or more mixing features for distributing oxygen within a liquid phase boiling reaction mixture. Typically, the mixing feature comprises one or more impellers mounted on a rotatable or otherwise movable shaft. For example, impellers may extend from a rotatable central vertical shaft Reactors may be constructed of materials designed to withstand the particular temperatures, pressures and reaction compounds used. Generally, suitable oxidation reactors are constructed using inert, corrosion-resistant materials such as titanium or may be lined with materials such as titanium or glass to improve resistance to corrosion and other deleterious effects. For example, titanium and glass, or other suitable corrosion resistant material are used for reactors and some other process equipment for the production of terephthalic acid from paraxylene using a solvent comprising acetic acid and a catalyst system which includes a bromine promoter under typical reaction conditions due to corrosivity of the acid solvent and certain reaction products, for example methyl bromide.

A source of molecular oxygen is also introduced into the reaction zone. Typically, an oxidant gas is used as a gaseous source of molecular oxygen. Air is conveniently used as a source of molecular oxygen. Oxygen-enriched air, pure oxygen and other gaseous mixtures comprising molecular oxygen, typically at least about 10 vol. %, also are useful. As will be appreciated, as molecular oxygen content of the source increases, compressor requirements and handling of inert gases in reactor off-gases are reduced. The source of molecular oxygen may be introduced into the reaction zone in one or more locations and is typically introduced in such a manner as to promote contact between the molecular oxygen and the other reaction compounds. Commonly, an oxidant gas is introduced in the lower portion of an oxidation reaction vessel and is distributed by mixing features such as one or more impellers mounted on a rotating shaft. Molecular oxygen content of oxidant gas varies but typically will range from about 5 to about 100 vol % molecular oxygen. To avoid the formation of potentially explosive mixtures, oxidant gas is generally added such that unreacted oxygen in the vapor phase above the liquid reaction mixture in the reaction zone is below the flammable limit. Keeping oxygen content of such vapor phase below the flammable limit depends upon the manner and rate of oxygen introduction, reaction rate (which is impacted by reaction conditions) and off-gas withdrawal. Typically, oxidant gas is supplied in an amount in relation to such operating parameters such that the vapor phase above the reaction mixture contains about 0.5 to about 8 vol. % oxygen (measured on a solvent-free basis).

Proportions of the feed, catalyst, oxygen and solvent are not critical to the invention and vary not only with choice of feed materials and intended product but also choice of process equipment and operating factors. Solvent to feed weight ratios suitably range from about 1:1 to about 30:1. Oxidant gas typically is used in at least a stoichiometric amount based on feed but not so great that unreacted oxygen in the vapor phase above the liquid reaction would exceed the flammable limit. Catalysts suitably are used in concentrations of catalyst metal, based on weight of aromatic hydrocarbon feed and solvent, greater than about 100 ppmw, preferably greater than about 500 ppmw, and less than about 10,000 ppmw, preferably less than about 6,000 ppmw, more preferably less than about 3000 ppmw. Preferably a halogen promoter, more preferably bromine, is present in an amount such that the atom ratio of halogen to catalyst metal suitably is greater than about 0.1:1, preferably greater than about 0.2:1 and suitably is less than about 4:1, preferably less than about 3:1. The atom ratio of halogen to catalyst metal most preferably ranges from about 0.25:1 to about 2:1.

Oxidation of aromatic hydrocarbon feed materials to product comprising aromatic carboxylic acid is conducted under oxidation reaction conditions. The reaction is operated at temperatures sufficient to drive the oxidation reaction and provide desirable purity while limiting solvent burning. Heat generated by oxidation is dissipated to maintain reaction conditions. Typically, heat of reaction is dissipated by boiling the reaction mixture and removing vapors resulting from boiling from the reaction zone. Generally suitable temperatures are in excess of about 120° C., preferably in excess of 140° C., and less than about 250° C. preferably less than about 230° C. Reactions temperatures of between about 145° C. to about 230° C. are typical in the production of several aromatic carboxylic acids, for example, terephthalic acid, benzoic acid and naphthalene dicarboxylic acid. At temperatures lower than about 120° C. the oxidation reaction can proceed slowly resulting in insufficient product purity and undesirably low conversion. For example, oxidation of paraxylene to produce terephthalic acid at a temperature less than about 120° C. can take more than 24 hours to proceed to substantial completion. The resultant terephthalic acid product may require significant additional processing due to its high level of impurities. At temperatures above 250° C., significant loss of solvent can occur due to solvent burning.

The oxidation reaction is conducted at a pressure at least high enough to maintain a substantial liquid phase comprising feed and solvent in the vessel. Generally, pressures of about 5 to about 40 $kg/cm^2$ gauge are suitable, with preferred pressures for particular processes varying with feed and solvent compositions, temperatures and other factors but typically between about 10 to about 30 $kg/cm^2$. Residence times in the reaction zone can be varied as appropriate for given throughputs and conditions, with about 20 to about 150 minutes being generally suited to a range of processes. For processes in which the aromatic acid product is substantially soluble in the reaction solvent, such as in the manufacture of trimellitic acid by oxidation of psuedocumene in acetic acid solvent, solid concentrations in the liquid body are negligible. In other processes, such as oxidation of xylenes to terephthalic or isophthalic acids using acetic acid and water as solvent for the reaction mixture, solids contents can be as high as about 50 wt. % of the liquid reaction body, with levels of about 10 to about 35 wt. % being more typical. As will be appreciated by those skilled in the manufacture of aromatic acids, preferred conditions and operating parameters vary with different products and processes and can vary within or even beyond the ranges specified above.

Aromatic carboxylic acid reaction product slurried or dissolved in a portion of the liquid reaction mixture from the liquid phase oxidation can be treated using conventional techniques to recover aromatic carboxylic acid reaction product contained therein. Typically, aromatic carboxylic acid product and by-products of the feed material slurried, dissolved or slurried and dissolved in liquid reaction mixture are removed from the reaction zone and recovered by suitable techniques. Thus, liquid phase oxidation according can comprise, in addition to the oxidation reaction step, a step comprising recovering from a liquid phase oxidation reaction mixture a product comprising aromatic carboxylic acid and impurities comprising reaction by-products. The product preferably is recovered as a solid product.

Soluble product dissolved in the liquid can be recovered by crystallization, which usually is accomplished by cooling and releasing pressure on a liquid slurry or solution from the oxidation reaction zone. Solid product slurried in the liquid and solids crystallized from reaction liquid or from crystallization solvents are conveniently separated from the liquids by centrifuging, filtration or combinations thereof. Solid products recovered from the reaction liquid by such techniques comprise aromatic carboxylic acid and impurities comprising by-products of the aromatic feed material. Liquid remaining after recovery of solid product from the liquid reaction mixture, also referred to as oxidation mother liquor, comprises solvent monocarboxylic acid, water, catalyst and promoter, soluble by-products of the liquid phase oxidation and impurities that may be present such as from recycle streams. The oxidation mother liquor normally also contains minor amounts of aromatic carboxylic acid and partial or intermediate oxidation products of the aromatic feed material remaining unrecovered from the liquid. The mother liquor is preferably returned at least in part to the reaction zone of at least one liquid phase oxidation so that components thereof that are useful in the liquid phase reaction, such as catalyst, promoter, solvent and by-products convertible to the desired aromatic carboxylic acid are re-used.

In preferred embodiments of the invention, a liquid phase reaction product mixture from oxidation comprising aromatic carboxylic acid and by-products of a liquid phase oxidation reaction is recovered from the liquid by crystallization in stages, such as in a series of crystallization vessels, with sequential reductions in temperature and pressure from earlier to later stages to increase product recovery. Crystallization in two to four stages, for example from an oxidation reaction temperature in the range of about 140 to about 250° C. and pressure in the range of about 5 to about 40 kg/cm$^2$ gauge to a final crystallization temperature in the range of about 110 to about 150° C. and pressure of ambient to about 3 kg/cm$^2$, provides substantial crystallization of solid aromatic carboxylic acid product. Oxidation mother liquor separated from the solid product by crystallization can be returned to the reaction zone as described above. Heat is removed from the vessels used for crystallization by removal of a gas phase formed as a result of flashing or other pressure letdown of the reaction product mixture, with a vapor phase removed from one or more stages preferably condensed and, directly or indirectly through one or more additional recovery stages, as discussed below, returned at least in part to the reaction zone for use in liquid phase oxidation.

Solid product recovered from the liquid phase oxidation, typically comprising aromatic carboxylic acid and impurities comprising oxidation by-products such as intermediate oxidation products of the aromatic feed material, can be separated from liquid oxidation mother liquor resulting from recovery of the solid product by any suitable technique. Examples include centrifuging, vacuum filtration, pressure filtration and filtration using belt filters. The resulting solid product is preferably washed after separation with liquid comprising water such as pure water or a wash liquid comprising minor amounts of solvent monocarboxylic acid, catalyst, aromatic feedstock, oxidation by-products or combinations thereof that can be beneficially recycled to oxidation, either directly or combined with other liquids such as oxidation mother liquor recycle or other liquids returned to the reaction zone. Separation of solid impure aromatic carboxylic acid recovered from an oxidation mother liquor and washing of solid product can be conveniently accomplished by solvent exchange filtration under pressure using pressure filters such as are disclosed in U.S. Pat. No. 5,679,846, and U.S. Pat. No. 5,200,557. A preferred filtration device for such separations is a BHS Fest filter as described more fully in U.S. Pat. No. 5,200,557.

Oxidation mother liquor and wash liquids removed from the filtered cake can be transferred directly or indirectly to liquid phase oxidation. Filtration and washing of the solid product in multiple stages and with increasingly pure wash liquids, for example liquids removed from filter cake in downstream stages as wash liquid in prior stages, can provide additional benefit by concentrating solvent monocarboxylic acid displaced from filtered solids for return to oxidation. In a more specific embodiment, the filtered cake wet with wash liquid resulting from such positive displacement filtration is directed from a final wash stage to a drying stage wherein it is optionally contacted with inert gas, typically under light to moderate pressure, for substantial removal of residual liquid from the cake. After washing and substantial removal of wash liquid from solid product comprising aromatic carboxylic acid and by-products, the resulting solid can be dried and directed to storage or other steps, which may include preparation of a reaction solution for purification of the solid product. Preferably, levels of residual solvent monocarboxylic acid in solid product directed to purification are about 5000 parts per million by weight ("ppmw") or less. Solid product can be dried with a flowing stream of nitrogen or other inert gas to reduce residual solvent levels.

The vapor phase above the liquid reaction mixture in the reaction zone (also referred to as the reaction overhead vapor or reaction vapor phase) comprises solvent and water. The overhead vapor also may contain unreacted oxidant gas, gaseous reaction byproducts, such as carbon oxides, vaporized reaction by-products such as methyl bromide, catalyst, or a combination thereof. If air is used as the oxidant gas, then the reaction overhead vapor typically comprises solvent, water, excess oxygen (if any), carbon oxides, nitrogen gas and reaction by-products.

A portion of the reaction vapor phase is transferred from the reaction zone to a separation zone in which a high efficiency separation of solvent from water in the reaction overhead vapor is performed. As used herein, "high efficiency separation" means separation of components primarily comprising reaction solvent from reaction overhead vapor such that at least about 95 wt % of the reaction solvent present in the reactor overhead vapor is removed. Preferably, the high efficiency separation is performed such that reaction solvent content of a high pressure gaseous overhead stream formed by high efficiency separation is not more than about 5 wt %, more preferably not more than about 2 wt %, most preferably not more than about 1 wt % of the reaction solvent present in the reaction overhead vapor. High efficiency separation helps reduce solvent loss and helps reduce the amount of make-up solvent used in the reaction. High efficiency separation also allows substantial retention of water in a gaseous phase useful for energy recovery. Such high efficiency separation results in a liquid bottoms stream, all or a portion of which is typically returned to the reaction zone to provide makeup solvent, and a high pressure gaseous overhead stream. The liquid bottoms stream is predominantly comprised of solvent. The liquid bottoms stream can also contain some heavy impurities, byproducts, catalyst, water or a combination thereof. Preferably, the liquid bottoms stream contains less than 35 wt % water, more preferably less than 25 wt % water. Such high efficiency separation is conducted at a pressure such that the high pressure gaseous overhead stream has a pressure of at least about 80%, preferably at least about 90%, more preferably at least about 95%, of the reaction pressure. Persons of skill in the art will appreciate that high efficiency separation could be performed at a pressure greater than reaction pressure but that, as a practical matter, such high efficiency separation is preferably conducted at a pressure such that the high pressure gaseous overhead stream has a pressure of at most about 100% of reaction pressure. Pressure rating of equipment of the separation zone preferably is at least about 80%, more preferably about 90 to about 110%, of the rating of the oxidation reaction vessel or zone of the oxidation step of the invented process from which the vapor phase is directed to separation.

The reaction vapor phase can be transferred from the reaction zone of a liquid phase oxidation to the separation zone directly, as where a separation device is mounted directly or in close association with an oxidation reaction vessel or other reaction zone, or indirectly, for example by means suitable conduits, valves, pumps and the like for effecting transfer. A minor portion of the high pressure and high temperature reaction vapor phase from the liquid phase oxidation may be directed to other uses, such as generation of high pressure steam or heat exchange fluid. Preferably, the vapor phase transferred to the separation device remains at high enough temperature and pressure so that energy content of the reaction vapor phase entering the separation zone is at least substantially retained and the reaction vapor phase provides sufficient heat for separation in contact with reflux liquid supplied to the separation zone. Most preferably, transfer of the reaction vapor phase to the separation zone is achieved by passage directly from the reaction zone or through suitable pressure rated piping such that temperature of the vapor phase entering the separation zone is no more than about 10° C. cooler than the reaction temperature in the liquid phase oxidation and pressure of the reaction vapor phase entering the separation zone is no more than about 3 kg/cm$^2$ less than the pressure in the liquid phase oxidation.

The separation zone for reaction vapor phase treatment according to the invention can comprise any device suitable for substantially separating solvent monocarboxylic acid from water in the high temperature and pressure reaction vapor phase removed from the liquid phase oxidation and present in the device at high temperature and pressure to obtain a liquid bottoms stream rich in solvent monocarboxylic acid and a high pressure gaseous overhead stream comprising water, as described above. Preferred separation devices are various columns or towers, often referred to as distillation columns and towers, dehydration towers, rectifying columns, water removal columns and high efficiency separation devices, that are designed for contact between gas and liquid phases flowing therethrough for mass transfer between the phases in a plurality of theoretical equilibrium stages, also sometimes referred to as "theoretical plates," such that the gas phase is separated or apportioned into fractions with various boiling ranges such that a liquid phase rich in at least one higher boiling component, such as the solvent monocarboxylic acid in the invented process, condenses from the vapor phase leaving a gas substantially depleted of such higher boiling component and comprising one or more lower boiling species, such as the water of the oxidation reaction vapor phase in the invented process. Temperature of the high pressure vapor phase removed from oxidation normally is high enough that there is no need for reboiling capability beyond that provided by the liquid phase oxidation reaction. Countercurrent flow of gas and liquid phases, such as by introducing a gas phase at a lower portion of the device and reflux liquid at an upper portion, is preferred for promoting contact between gas and liquid phases in the separation device. Contact also is promoted by internal structure providing surface for gas-liquid contact. For example, in a preferred embodiment, the separation zone includes a distillation column containing high efficiency packing, or sieve, valve or bubble cap trays is used. An example of a commercially available high efficiency packing which can be used in a high efficiency distillation column is Koch FLEXIPAC, available from KGGP LLC. Preferably such distillation column has at least about 30 theoretical stages, more preferably at least about 50 theoretical stages. Reflux for such distillation columns can include mother liquor from other compatible processes, for example mother liquor from aromatic carboxylic acid purification processes.

Reflux liquid comprising water is supplied into contact with the high pressure reaction vapor phase in the separation zone. Any suitable source of liquid comprising water and substantially free of impurities detrimental to separation can be utilized. Preferred sources of reflux liquid include liquids condensed from high pressure gases removed from separation and/or condensing zones according to the invented process. In a more preferred embodiment described more fully herein, a purification mother liquor obtained in recovery of a purified aromatic carboxylic acid product from a purification liquid reaction mixture is directed to separation such that reflux liquid supplied to the separation zone comprises the purification mother liquor. Reflux liquid preferably is supplied at a rate and temperature effective to quench heat of the liquid phase oxidation reaction transferred to the separation zone in the reaction vapor phase from the oxidation. When the separation zone is coupled to a reaction vessel from liquid phase oxidation for substantially direct transfer of reaction vapor phase from oxidation to separation the reaction vessel functions as reboiler. In such embodiments, the rate at which liquid reflux is supplied to the separation zone is conveniently expressed as weight of liquid provided to the zone relative to weight of aromatic hydrocarbon feed material introduced to the liquid phase oxidation. Preferably, reflux liquid provided to the separation zone according to the invented process is at a temperature in the range of about 120 to about 170° C. and more preferably at about 130 to about 160° C. At such temperatures, liquid preferably is supplied to separation at a rate of about 4 to about 5 weights of the liquid per weight of aromatic hydrocarbon precursor introduced to the liquid phase oxidation.

The separation zone according to the invention can comprise a single device or multiple devices, such as towers, columns or other structure, in series. When using two or more devices in series, they are configured, and their respective inlets and outlets communicate such that high pressure reaction vapor phase removed from the oxidation reaction vessel flows into and through the series with separation therein of water from C1-8 monocarboxylic acid in the high pressure reaction vapor phase and reverse flows of liquid, including reflux and solvent monocarboxylic acid-rich liquid separated from the high pressure reaction vapor phase, within or between devices such that liquid rich in solvent monocarboxylic acid but lean in water can be withdrawn, preferably from a first device in the series and a high pressure gaseous overhead stream from the separation comprising water vapor and substantially free of low-molecular weight monocarboxylic acid solvent can be removed, preferably from the last device in the series.

A high pressure gaseous overhead stream is drawn from the separation zone. Optionally other streams can be drawn from the separation zone or from the high pressure gaseous overhead stream o. Such other streams may be used elsewhere in the process, for example they may be directed to downstream or upstream equipment, or can be used in other processes, for example, to provide high pressure steam or to extract heat. Typically, the high pressure gaseous overhead stream exits the separation zone at a temperature greater than about 100° C., preferably greater than about 120° C., and less than about 250° C., preferably less than about 230° C., and at a pressure in the range of about 4 to about 40 kg/cm$^2$ gauge. Generally, the temperature at which the high pressure gaseous overhead stream exits the separation zone is from about 0° C. to about 20° C. less than the temperature of the oxidation reactor, preferably from about 5° C. to about 15° C. less than the temperature of the oxidation reactor. Generally, the pressure at which the high pressure gaseous overhead stream exits the separation zone is from about 0 to about 1 kg/cm$^2$ gauge less than the pressure of the oxidation reactor.

The high pressure gaseous overhead stream comprises a major portion of water, typically greater than about 35 wt %, preferably at least 50 wt %, more preferably at least 70 wt % of the water present in the reaction overhead vapor. Preferably, the high pressure gaseous overhead stream comprises at least about 60 vol % water, preferably at least about 65 vol % water. Typically, the high pressure gaseous overhead stream may also contain carbon oxides, nitrogen gas, unconsumed molecular oxygen and oxidation reaction byproducts such as alkyl bromides.

High pressure gaseous overhead stream obtained from the separation zone is directed to a condensing zone where heat energy is extracted from the high pressure gaseous overhead stream. The condensing zone can comprise any means effective for condensing water substantially free of organic impurities from the high pressure gas introduced to the condensing zone which also allows for extraction of heat energy, preferably without substantially reducing pressure so as to reduce energy loss. Preferably, the condensing zone includes one or more condenser or heat exchange means effective for providing indirect heat transfer between the high pressure gaseous overhead stream and a suitable heat sink material, and preferably a heat exchange fluid. A single device or a plurality of devices in series can be employed. Shell and tube heat exchangers and kettle type condensers are examples of preferred devices. Preferably, all or substantially all of the high pressure gaseous overhead stream from separation is directed to the condensing zone to enable substantial recovery of both energy and materials therefrom. Cooling preferably is conducted under conditions such that a condensing zone off-gas under pressure not substantially reduced from that of the high pressurize gas introduced to the condensing zone remains after condensing the liquid condensate and is withdrawn from the condensing zone. The condensing zone off-gas comprises water, incondensable components of the high pressurize gas from the separation zone, gaseous reaction by-products and minor amounts of aromatic feed material and most preferably is at a temperature of about 50 to about 150° C. and under pressure that is no more than about 3 kg/cm$^2$ less than the pressure of the inlet gas to the condensing zone. More preferably, the pressure differential between a gas removed from the separation device and the condensing zone off-gas after condensation of liquid condensate is about 2 kg/cm$^2$ or less and most preferably about 0.5 to about 1 kg/cm$^2$.

Heat energy is extracted from high pressure gaseous overhead stream in the condensing zone by heat exchange with a heat sink material which serves to heat the heat sink material. The heat sink material preferably is a heat sink fluid, and most preferably water. When using water as the heat exchange fluid, heat exchange with the high pressurize gas from separation preferably converts the water to steam which can be directed to other parts of the invented process for heating or to uses outside the process. Similarly, heat can be extracted from high pressure gaseous overhead stream by heat exchange with liquids from other process steps. In a preferred embodiment of the invented process, heat energy is extracted from high pressure gaseous overhead stream by heat exchange with a heat exchange fluid comprising water and is conducted in a series of heat exchangers operated at successively cooler temperatures such that steam at different pressures is generated from the heat exchange water. Steam at different pressures is preferably directed to one or more process steps in which steam under corresponding pressure or pressures is useful for heating, while liquid condensate comprising water at successively lower temperatures is generated in the series of heat exchangers.

Heat energy extraction in the condensing zone can be conducted in a single step. It also can be conducted in multiple steps in which a gas stream comprising high pressure gaseous overhead stream removed from a separation zone is cooled to a first temperature in a first stage to yield a first stage condensate liquid and an uncondensed portion of the gas which is subsequently condensed at a lower temperature in a second stage to provide a second stage condensate liquid and an uncondensed portion of the gas introduced to the second stage, and optionally one or more additional stages in which an uncondensed portion of gas from a prior stage is condensed at a lower temperature than in the previous stage to form a liquid condensate and a remaining uncondensed gaseous portion. Heat energy extracted from the high pressure gaseous overhead stream by heat exchange between the pressurized gas and uncondensed portions thereof in the staged condensers provides heat exchange fluid at different temperatures or pressures, for example moderate and low pressure steam, which can be used for heating in other process steps or outside the process. In preferred embodiments of the invention, two or more levels of steam are produced for energy recovery, which is conveniently accomplished using a condensing or other low pressure steam turbine. In such embodiments, condensate liquid removed at different temperatures can be directed to other process uses with corresponding temperatures, thereby avoiding additional heating or cooling of the condensate portions.

Condensate liquid recovered at higher temperatures, for example in the range of about 130 to about 160° C., also are well suited for reflux to the separation zone as such or in combination with aqueous liquids from other process steps such as mother liquor remaining after recovery and/or separation of purified aromatic carboxylic acid in a purification step. Lower temperature condensates, for example those in the range of about 60 to about 90° C., are also well suited for hot condensate uses such as wash liquids for product separations and seal flush liquids in liquid phase oxidation and still cooler condensate, for example in the range of about 40 to about 50° C., for cold condensate uses such as scrubber washes. Some uses for the condensate may involve treatment of the stream to remove impurities or otherwise alter the composition or condition of the condensate.

Heat energy is extracted in the condensing zone such that only a portion of the water in the high pressure gaseous overhead stream is condensed in the condensing zone. Such partial condensation operates such that a condensate is formed in the condensing zone from the high pressure gaseous overhead stream having less than about 60 wt % of the water in the high pressure gaseous overhead stream, preferably less than about 50 wt % of the water, and more than about 20 wt % of the water in the high pressure gaseous overhead stream, preferably more than about 30 wt %. The effectiveness of heat exchange as an energy recovery method decreases as each additional incremental wt % of water is condensed. Partial condensation in these ranges allows for increased total energy recovery by avoiding the range in which the efficacy of heat exchange is substantially reduced. Partial condensation allows heat energy recovery from the high pressure gaseous overhead stream while leaving enough uncondensed water for further energy recovery in the form of work. Even though less energy is extracted through the partial condensation step itself, the uncondensed portion of the high pressure gaseous overhead stream retains significant energy which can be recovered as work such that the total energy recovered from both is greater than the energy recovered from complete condensation processes or from processes using only energy recovery in the form of work. The extracted heat can be used elsewhere in the process or in related processes.

The portion of the high pressure gaseous overhead not condensed in the condensing zone, referred to herein as high pressure off-gas, retains from about 40 wt % to about 80 wt % of the water from the high pressure overhead gaseous stream. The high pressure off-gas is sent, directly or indirectly, to an expansion zone where energy is recovered from the high pressure off-gas in the form of work. The expansion zone includes one or more devices for recovering energy as work, preferably isentropically, more preferably one or more expanders or similar apparatuses. As will be appreciated by those of skill in the art, isentropic devices are not truly isentropic and, as a practical matter, change in entropy does occur. However, preferably, the isentropic energy recovery employed has less than about 30% change in entropy, more preferably less than about 25% change in entropy, most preferably less than about 20% change in entropy. Work is extracted from the high pressure off-gas in the extraction zone and a vent gas stream of lower pressure than the high pressure off-gas is formed.

Work extracted from the high pressure off-gas in the expansion zone can be used, for example, to generate electricity using a generator or for operating equipment requiring mechanical work such as a compressor. Such extracted energy can be used elsewhere in the process, in other processes, can be stored, or delivered to an electrical grid for transmission to other locations.

In some embodiments, the apparatus according to this aspect of the invention comprises a reaction vessel rated for a first pressure and suitable for liquid phase oxidation of an aromatic hydrocarbon feed material with gaseous oxygen in a liquid phase reaction mixture comprising monocarboxylic acid solvent and water under conditions effective to maintain a liquid phase reaction mixture and generate a high pressure vapor phase and comprising at least one vent for removing a high pressure overhead vapor from the vessel; a high efficiency separation apparatus rated for a second pressure which is not substantially less than the first pressure and comprising at least one gas inlet in fluid communication with the reaction vessel for receiving a high pressure overhead vapor removed from at least one vent of the reaction vessel, at least liquid inlet for introducing reflux liquid to the high efficiency separation apparatus, at least one gas outlet for removing a high pressure gaseous overhead stream from the device, at least one liquid outlet for removing a liquid bottoms stream from the high efficiency separation apparatus and a fractionating zone disposed at a position intermediate at least one gas inlet and at least one gas outlet and capable of performing high efficiency separation of solvent monocarboxylic acid from water in the reactor overhead vapor received in the device such that a liquid bottoms stream comprising less than 35 wt % water, preferably less than 25 wt % water, a high pressure gaseous overhead stream comprising water and no more than 5 wt %, preferably not more than 2 wt %, more preferably not more than 1 wt % of solvent monocarboxylic acid present in the reactor overhead vapor are formed; condensing means comprising at least one gas inlet for receiving a high pressure gaseous overhead stream removed from at least one gas outlet of the separation device; heat exchange means for transfer of heat from a high pressure gaseous overhead stream in the condensing means to a suitable heat sink material such that a liquid condensate comprising from about 20 wt % to about 60 wt % of the water in the high pressure gaseous overhead stream is condensed from the high pressure gaseous overhead stream, a high pressure off-gas comprising from about 40 wt % to about 80 wt % of the water in the high pressure gaseous overhead stream is formed, and a suitable heat sink material at an increased temperature or pressure is formed; and expansion means for extracting energy in the form of work comprising at least one gas inlet for receiving the high pressure off-gas directly or indirectly from the condensing means and at least one gas outlet for expelling a vent gas stream at a pressure lower than inlet pressure.

The high pressure off-gas can be treated before extracting energy in the form of work. It will be appreciated that treatments can affect the amount of energy recoverable from the high pressure off-gas. Preferably, treatment or combinations of treatments, if used, are such that water in the high pressure off-gas is sufficiently gaseous in the extraction zone prior to work energy recovery such that the work energy recovery does not result in significant condensation of water. A combination of treatments can be used. For example, the high pressure off-gas can be treated for removing corrosive or combustible materials. Although any treatment for removing corrosive or combustible materials from the high pressure off-gas can be used, preferably without significant condensation of liquid water, preferably the high pressure off-gas is subjected to thermal oxidation treatment, more preferably catalytic thermal oxidation treatment. Such treatments generally comprise heating an uncondensed gas under pressure, and comprising exhaust gas under pressure removed from condensation or after scrubbing or other treatment, and gaseous oxygen in a combustion zone under pressure not substantially less than that of the pressurized gas and at elevated temperature effective to oxidize organic, combustible and corrosive components to a less corrosive or more environmentally compatible gas comprising carbon dioxide and water. Heating under pressure with oxygen gas preferably is conducted in the presence of a suitable oxidation catalyst disposed within the combustion zone so as not to interrupt flow of the pressurized gas therethrough. The pressurized gas can optionally be subjected to preheating before oxidation. Preheating can be accomplished by any suitable means such as by heat exchange, direct steam injection or other suitable means. Optionally, combustion treatment can also include scrubbing a pressurized gas removed from combustion to remove acidic, inorganic materials such as bromine and hydrogen bromide which are generated by oxidation of alkyl bromides present in the condenser exhaust gas when a bromine source is used for liquid phase oxidation as noted above.

Catalysts for catalytic oxidation generally comprise at least one transition group element of the Periodic Table (IUPAC). Group VIII metals are preferred, with platinum, palladium and combinations thereof and with one or more additional or adjuvant metals being especially preferred. Such catalyst metals may be used in composite forms such as oxides. Typically, the catalyst metals are disposed on a support or carrier material of lower or no catalytic activity but with sufficient strength and stability to withstand the high temperature and pressure oxidizing environment of the combustion zone. Suitable catalyst support materials include metal oxides comprising one or more metals, examples of which include mullite, spinels, sand, silica, alumina silica alumina, titania, zirconia. Various crystalline forms of such materials can be utilized, such as alpha, gamma, delta and eta aluminas, rutile and anatase titanias. Catalyst metal loadings on support compositions are suitably fractions to several percents by weight, with higher loadings being preferred for use when treating gases with significant water vapor content, such as about 20 vol. % or more. Catalysts can be used in any convenient configuration, shape or size. For example, the catalyst can be in the form of pellets, granules, rings, spheres, and the like and preferably may be formed into or disposed on a rigid cellular, honeycomb, perforated or porous structural configuration to promote contact with gases present in the combustion zone without impeding gas flow through the zone. Specific examples of catalytic oxidation catalysts for combustion treatment of exhaust gas removed from condensation in off-gas treatment according to the invention comprise about one-half to about one wt % palladium supported on an alumina monolith support.

The high pressure off-gas or a portion thereof can also optionally be heated to ensure that the water present in the high pressure off-gas is fully converted to steam prior to recovering energy in the form of work and to avoid condensation of water in the extraction zone which can be detrimental to apparatus employed. Such heating can take place before, after or in combination with any other treatments employed, for example, thermal catalytic oxidation. In such an embodiment, heating of the off-gas can be accomplished by any suitable means, such as a heat exchanger, direct steam injection or other means known in the art. Heating to about 200° C. or greater is generally effective for avoiding condensation of water in the expansion zone, with temperatures of about 250 to about 350° C. preferred.

Vent gas, obtained from the expansion zone formed when work energy is extracted from the high pressure off-gas, is preferably subjected to additional treatment, for example caustic scrubbing, to remove any compounds, for example bromine or other halogen compounds, which may be undesirable for atmospheric release. Water in the vent gas can be extracted and can be recycled, used in other processes, disposed of, subjected to further treatment or other uses as known in the art.

Past attempts to recover energy from high pressure gaseous overhead streams formed during liquid-phase oxidation of aromatic hydrocarbons in the production of aromatic carboxylic acids have either not employed a condenser or have employed complete condensation. Even in past energy recovery schemes which have employed condensation followed by expansion, only complete condensation was employed.

We have surprisingly found that recovering energy by subjecting a high pressure gaseous overhead stream to partial condensation wherein energy is extracted through heat exchange with an appropriate heat sink material and recovering work energy from the resulting high pressure off-gas results in the recovery of significantly greater amount of energy than methods which condense all or substantially all of the water in a high pressure stream or methods which primarily recover energy as work. By only partially condensing the water in the high pressure gaseous overhead stream, sufficient water remains in the high pressure off-gas exiting the condenser to allow beneficial energy recovery in the form of work.

Commercial efforts to extract energy from reactor overhead vapor formed during the production of aromatic carboxylic acids from aromatic hydrocarbons included recovering energy by substantially complete condensation followed by expansion of water-depleted off-gas, by work energy extraction alone, or by subjecting portions of high pressure gaseous overhead to each of such methods. Although certain of these methods can offer significant advantages, some commercially favorable embodiments of each of the foregoing methods do not result in significant differences in total energy recovery. Such results suggested that there would be no significant gain in energy by using a partial condensation followed by work energy extraction. Such results suggested that energy not recovered through condensation of the high pressure gaseous overhead stream would be roughly equal to energy recovered from subsequent work energy extraction. We have surprisingly found a significant increase in energy recovery by recovering energy from partially condensing the high pressure gaseous overhead stream and recovering additional energy from subsequent work energy extraction.

In a particular embodiment, the invention is used for the boiling liquid phase oxidation of an aromatic hydrocarbon feed comprising paraxylene to terephthalic acid. Liquid components comprising the aromatic hydrocarbon feed and solvent are continuously introduced into the reaction vessel. Catalyst and promoter, each most preferably also dissolved in solvent, are introduced into the reaction vessel. Acetic acid or aqueous acetic acid is a preferred solvent, with a solvent to feed ratio of about 2:1 to about 5:1 being preferred. The catalyst preferably comprises cobalt in combination with manganese, cerium, zirconium, hafnium, or any combination thereof and a bromine source. The catalyst is suitably present in amounts providing about 600 ppmw to about 2500 ppmw of catalyst metals based on weight of the aromatic hydrocarbon and solvent. The promoter most preferably is present in an amount such that the atom ratio of bromine to catalyst metal is about 0.4:1 to about 1.5:1. Oxidant gas, which is most preferably air, is supplied to the reactor vessel at a rate effective to provide at least about 3 to about 5.6 moles molecular oxygen per mole of aromatic hydrocarbon feed material so that the reactor overhead vapor contains from about 0.5 to about 8 vol. % oxygen (measured on a solvent-free basis).

In such particular embodiment, the reaction vessel is preferably maintained at about 150 to about 225° C. under pressure of about 5 to about 40 kg/cm² gauge. Under such conditions, contact of the oxygen and feed material in the liquid body results in formation of solid terephthalic acid crystals, typically in finely divided form. Solids content of the boiling liquid slurry typically ranges up to about 40 wt. % and preferably from about 20 to about 35 wt. %, and water content typically is about 5 to about 20 wt. % based on solvent weight. Boiling of the liquid body for control of the reaction exotherm causes volatilizable components of the liquid body, including solvent and water of reaction, to vaporize within the liquid. Unreacted oxygen and vaporized liquid components escape from the liquid into the reactor space above the liquid. Other species, for example nitrogen and other inert gases that are present if air is used as an oxidant gas, carbon oxides, and vaporized by-products, e.g., methyl acetate and methyl bromide, also may be present in the reactor overhead vapor.

Aromatic carboxylic acid reaction product, slurried or dissolved in a portion of the liquid body, is removed from the vessel. The product stream can be treated using conventional techniques to separate its components and to recover the aromatic carboxylic acid contained therein, usually by crystallization, liquid-solid separations and drying. Conveniently, a slurry of solid product in the liquid is centrifuged, filtered or both, in one or more stages. Soluble product dissolved in the liquid can be recovered by crystallization. Liquid comprising water, solvent, unreacted feed material, and often also containing one or more liquid catalyst, promoter and reaction intermediates, can be returned to the reaction vessel.

Aromatic carboxylic acid product recovered from the liquid can be used or stored as is, or it may be subjected to purification or other processing. Purification is beneficial for removing by-products and impurities that may be present with the aromatic carboxylic acid that is recovered. For aromatic carboxylic acids such as terephthalic and isophthalic acids, purification preferably involves hydrogenation of the oxidation product, typically dissolved in water or other aqueous solvent, at elevated temperature and pressure in the presence of a catalyst comprising a metal with hydrogenation catalytic activity, such as ruthenium, rhodium, platinum or palladium, which typically is supported on carbon, titania or other suitable, chemically-resistant supports or carriers for the catalyst metal. Purification processes are known, for example, from U.S. Pat. No. 3,584,039, U.S. Pat. No. 4,782, 181, U.S. Pat. No. 4,626,598 and U.S. Pat. No. 4,892,972. If purification is conducted with water as solvent, washing with water to remove residual oxidation solvent from the solid aromatic carboxylic acid can be carried out as an alternative to drying. Such washing can be accomplished using suitable solvent exchange devices, such as filters, as disclosed in U.S. Pat. No. 5,679,846, and U.S. Pat. No. 5,175,355. Optionally, all or a portion of mother liquor from purification processes may be sent, directly or indirectly, to the high efficiency separation apparatus. For example, if one or more high efficiency distillation columns are used to perform the high efficiency separation, all or a portion of the purification mother liquor can be used as reflux for one or more of such high efficiency distillation columns.

Typically, oxidation mother liquor is separated from the unpurified aromatic carboxylic acid product through separation techniques known in the art, for example, filtration, centrifuge, or combinations of known methods. It is preferable to recycle at least a portion of the mother liquor and commercial operations typically recycle a significant portion of the mother liquor. For example, such mother liquor can be recycled directly or indirectly to the oxidation reactor or the high efficiency separation apparatus. Mother liquor can be separated from purified aromatic carboxylic acid product through similar techniques and such mother liquor may be recycled for use in other stages of this process or in other processes.

In greater detail, a preferred purification step according to the invention comprises dissolving in a liquid comprising water and solid product comprising aromatic carboxylic acid and impurities to form a purification reaction solution, contacting the purification solution at elevated temperature and pressure with hydrogen in the presence of a hydrogenation catalyst to form a purification liquid reaction mixture, recovering from the purification liquid reaction mixture a solid purified product comprising aromatic carboxylic acid with reduced levels of impurities and separating an aqueous liquid purification mother liquor comprising oxidation by-products, hydrogenation products thereof and combinations thereof from the recovered solid purified product. Hydrogenation of impure aromatic carboxylic acids to reduce impurities levels is conducted with the impure acid in aqueous solution.

Concentrations in the purification solvent of impure aromatic carboxylic acid to be treated in a purification step generally are low enough that the impure acid is substantially dissolved and high enough for practical process operations and efficient use and handling of liquid used as solvent and remaining as purification mother liquor after recovery of a pure form of aromatic carboxylic acid with reduced impurities from purification reaction mixtures. Suitably, solutions comprising about 5 to about 50 parts by weight impure aromatic carboxylic acid per hundred parts by weight solution at process temperatures provide adequate solubility for practical operations. Preferred purification reaction solutions contain about 10 to about 40 wt %, and more preferably about 20 to about 35 wt %, impure aromatic carboxylic acid at the temperatures used for purification by catalytic hydrogenation.

Catalysts suitable for use in purification hydrogenation reactions comprise one or more metals having catalytic activity for hydrogenation of impurities in impure aromatic carboxylic acid products, such as oxidation intermediates and by-products and/or aromatic carbonyl species. The catalyst metal preferably is supported or carried on a support material that is insoluble in water and unreactive with aromatic carboxylic acids under purification process conditions. Suitable catalyst metals are the Group VIII metals of the Periodic Table of Elements (IUPAC version), including palladium, platinum, rhodium, osmium, ruthenium, iridium, and combinations thereof. Palladium or combinations of such metals that include palladium are most preferred. Carbons and charcoals with surface areas of several hundreds or thousands $m^2/g$ surface area and sufficient strength and attrition resistance for prolonged use under operating conditions are preferred supports. Metal loadings are not critical but practically preferred loadings are about 0.1 wt % to about 5 wt % based on total weight of the support and catalyst metal or metals. Preferred catalysts for conversion of impurities present in impure aromatic carboxylic acid products comprising crude terephthalic acid obtained by liquid phase oxidation of a feed material comprising paraxylene contain about 0.1 to about 3 wt % and more preferably about 0.2 to about 1 wt % hydrogenation metal. For such uses, the metal most preferably comprises palladium.

For practical applications, catalyst is most preferably used in particulate form, for example as pellets, extrudate, spheres or granules, although other solid forms also are suitable. Particle size of the catalyst is selected such that a bed of catalyst particles is easily maintained in a suitable purification reactor but permits flow of the purification reaction mixture through the bed without undesirable pressure drop. Preferred average particle sizes are such that catalyst particles pass through a 2-mesh screen but are retained on a 24-mesh screen (U.S. Sieve Series) and, more preferably, through a 4-mesh screen but with retention on a 12-mesh and, most preferably 8-mesh, screen.

Contacting aqueous purification reaction solution with hydrogen in the presence of catalyst for purification is conducted at elevated temperatures and pressures. Temperatures range from about 200 to about 370° C., with about 225 to about 325° C. being preferred and about 240 to about 300° C. being most preferred. Pressure is at a level sufficient to maintain a liquid phase comprising the aqueous reaction solution. Total pressure is at least equal to, and preferably exceeds, the sum of the partial pressures of the hydrogen gas introduced to the process and water vapor that boils off from the aqueous reaction solution at the temperature of operation. Preferred pressures are about 35, and more preferably about 70, to about 105 kg/cm$^2$.

The aqueous purification reaction solution is contacted with hydrogen gas under hydrogenation conditions as described above in a suitable reaction vessel capable of withstanding reaction temperatures and pressures and also the acidic nature of its liquid contents. A preferred reactor configuration is a cylindrical reactor with a substantially central axis which, when the reactor is positioned for process use, is vertically disposed. Both upflow and downflow reactors can be used. Catalyst typically is present in the reactor in one or more fixed beds of particles maintained with a mechanical support for holding the catalyst particles in the bed while allowing relatively free passage of reaction solution therethrough. A single catalyst bed is often preferred although multiple beds of the same or different catalyst or a single bed layered with different catalysts, for example, with respect to particle size, hydrogenation catalyst metals or metal loadings, or with catalyst and other materials such as abrasives to protect the catalyst, also can be used and may provide benefits. Mechanical supports in the form of flat mesh screens or a grid formed from appropriately spaced parallel wires are commonly employed. Other suitable catalyst retaining means include, for example, a tubular Johnson screen or a perforated plate. Internal components and surfaces of the reactor and the mechanical support for the catalyst bed are constructed of materials that are suitably resistant to corrosion from contact with the acidic reaction solution and reaction product mixture. Most suitably, supports for catalyst beds have openings of about 1 mm or less and are constructed of metals such as stainless steel, titanium or Hastelloy C.

In preferred embodiments of the invention, aqueous solution of impure aromatic carboxylic acid to be purified is added to the reactor vessel at elevated temperature and pressure at a position at or near the top portion of the reactor vessel and the solution flows downwardly through the catalyst bed contained in the reactor vessel in the presence of hydrogen gas, wherein impurities are reduced with hydrogen, in many cases to hydrogenated products with greater solubility in the reaction mixture than the desired aromatic carboxylic acid or with less color or color-forming tendencies. In such a preferred mode, a liquid purification reaction mixture comprising aromatic carboxylic acid and hydrogenated impurities is removed from the reactor vessel at a position at or near a lower portion or bottom of the reactor.

Reactors used for purification may be operated in several modes. In one mode, a predetermined liquid level is maintained in the reactor and, for a given reactor pressure, hydrogen is fed at a rate sufficient to maintain the predetermined liquid level. The difference between the actual reactor pressure and the vapor pressure of the vaporized purification solution present in the reactor head space is the hydrogen partial pressure in the head space. Alternatively, hydrogen can be fed mixed with inert gas such as nitrogen or water vapor, in which case the difference between the actual reactor pressure and the vapor pressure of the vaporized reaction solution present is the combined partial pressure of hydrogen and the inert gas mixed therewith. In such cases hydrogen partial pressure may be calculated from the known relative amounts of hydrogen and inert gas present in the mixture.

In another operating mode, the reactor can be filled with the aqueous liquid reaction solution so that there is essentially no reactor vapor space but a hydrogen bubble at the top or in the head of the reactor that expands or contracts in size to provide volume in the reactor head so that hydrogen added to the reactor is dissolved into the incoming purification reaction solution. In such an embodiment, the reactor is operated as a hydraulically full system with dissolved hydrogen being fed to the reactor by flow control. The concentration of hydrogen in solution may be modulated by adjusting the hydrogen flow rate to the reactor. If desired, a pseudo-hydrogen partial pressure value may be calculated from the solution hydrogen concentration which, in turn, may be correlated with the hydrogen flow rate to the reactor.

When operating such that process control is effected by adjusting the hydrogen partial pressure, the hydrogen partial pressure in the reactor is preferably in the range of about one-half to about 15 kg/cm$^2$ gauge or higher, depending on pressure rating of the reactor, impurities levels of the impure aromatic carboxylic acid, activity and age of the catalyst and other considerations known to persons skilled in the art. In operating modes involving directly adjusting hydrogen concentration in the feed solution, the solution usually is less than saturated with respect to hydrogen and the reactor itself is hydraulically full. Thus, an adjustment of the hydrogen flow rate to the reactor will result in the desired control of hydrogen concentration in the solution.

Space velocity, expressed as weight of the impure aromatic acid in the purification reaction solution per weight of catalyst per hour, during hydrogenation is typically about 1 hours$^{-1}$ to about 25 hour$^{-1}$, and preferably about 2 hours$^{-1}$ to about 15 hours$^{-1}$. Residence time of the purification liquid stream in the catalyst bed varies depending on the space velocity.

Pure forms of aromatic carboxylic acid product with reduced levels of impurities relative to the crude or other impure aromatic carboxylic acid product used for preparing the purification solution is recovered from the liquid purification reaction mixture. The purification reaction mixture, comprising aqueous reaction solvent having dissolved therein aromatic carboxylic acid and hydrogenated aromatic impurities having greater solubility in the aqueous reaction liquid than their unhydrogenated precursors, is cooled to separate a pure form of solid aromatic carboxylic acid with reduced impurities from the reaction mixture, leaving a liquid purification mother liquor having hydrogenated impurities dissolved therein. Separation is commonly achieved by cooling to a crystallization temperature, which is sufficiently low for crystallization of the aromatic carboxylic acid to occur, thereby producing crystals within the liquid phase. The crystallization temperature is sufficiently high so that dissolved impurities and their reduction products resulting from hydrogenation remain dissolved in the liquid phase. Crystallization temperatures generally range up to 160° C. and preferably up to about 150° C. In continuous operations, separation normally comprises removing liquid purification reaction mixture from the purification reactor and crystallization of aromatic carboxylic acid in one or more crystallization vessels. When conducted in a series of stages or separate crystallization vessels, temperatures in the different stages or vessels can be the same or different and preferably decrease from each stage or vessel to the next. Crystallization typically also results in flashing of liquid from the purification liquid reaction mixture, which can be recovered and recycled to one or more of purification, one or more upstream crystallization stages or, in preferred embodiments of the invention, to separation of solvent monocarboxylic acid and water vapor in a high pressure vapor phase from liquid phase oxidation.

Thereafter, crystallized, purified aromatic carboxylic acid product is separated from the purification mother liquor, including hydrogenated impurities dissolved therein. Separation of the crystallized product is commonly conducted by centrifuging or by filtration. A preferred separation comprises pressure filtration of an aqueous slurry of pure forms of aromatic carboxylic acid and washing of filter cake resulting from filtration with a liquid comprising water as described in U.S. Pat. No. 5,175,355, which is incorporated herein by reference.

Purification mother liquor remaining after recovery of solid purified aromatic carboxylic acid from the purification reaction mixture comprises water and hydrogenated derivatives of by-products or impurities present in the impure aromatic carboxylic acid starting material. The mother liquor commonly also includes minor amounts of aromatic carboxylic acid that remain in solution. Such hydrogenated derivatives include compounds suitable for conversion to aromatic carboxylic acid by liquid phase oxidation and, accordingly, in preferred embodiments of the invention, at least a portion of such hydrogenated derivatives are transferred directly or indirectly to a liquid phase oxidation. Residual aromatic carboxylic acid present in the mother liquor also can be transferred directly or indirectly to liquid phase oxidation after separation from, or more preferably, together with, such hydrogenated derivatives. Transfer of such derivatives and aromatic carboxylic acid to oxidation is conveniently accomplished by directing at least a portion of a purification mother liquor remaining after separation of a solid pure form of aromatic carboxylic acid to a liquid phase oxidation step. Water content of purification mother liquor can upset water balance in oxidation unless water from purification mother liquor directed to oxidation is accounted for in other streams that may be returned to oxidation. Transfer of hydrogenated impurities in a purification mother liquor, alone or preferably in combination with aromatic carboxylic acid present in the mother liquor, to liquid phase oxidation is preferably accomplished without upsetting water balance in the oxidation. More preferably, at least a portion, and most preferably substantially all, of a liquid mother liquor remaining after separation of the solid purified aromatic carboxylic acid from the liquid purification reaction mixture is transferred directly or indirectly to a separation zone of off-gas treatment of a high pressure vapor phase removed from oxidation according to the invention where it is used as reflux liquid. For example, if one or more distillation columns are used for separation of solvent monocarboxylic acid and water in a high pressure vapor phase generated by liquid phase oxidation of aromatic feed material, purification mother liquor can be used in whole or in part as reflux for one or more columns. Water present in mother liquor added as reflux is substantially vaporized, entering the vapor phase in the tower, with water retained in the vapor phase that exits the tower becoming part of the pressurized gas from separation. Higher boiling components of the mother liquor, including hydrogenated impurities such as liquid phase oxidation by-products of the aromatic feed material for the oxidation and aromatic carboxylic acid if present, remain substantially in the liquid phase and can be returned directly or indirectly to a liquid phase oxidation reaction mixture, for example as part of the solvent monocarboxylic acid-rich liquid phase resulting from separation or in a stream separately removed from separation.

Purification reactor and catalyst bed configurations and operating details and crystallization and product recovery techniques and equipment useful in the process according to this invention are described in further detail in U.S. Pat. No. 3,584,039, U.S. Pat. No. 4,626,598, U.S. Pat. No. 4,629,715, U.S. Pat. No. 4,782,181 U.S. Pat. No. 4,892,972, U.S. Pat. No. 5,175,355, U.S. Pat. No. 5,354,898, U.S. Pat. No. 5,362,908 and U.S. Pat. No. 5,616,792 which are incorporated herein by reference.

FIG. 1 illustrates a preferred embodiment of this invention. A preferred form of apparatus, also represented in the figure, comprises a pressure rated reaction vessel that defines a substantially enclosed interior volume adapted to containing a liquid reaction mixture and a reaction vapor phase and comprising at least one inlet for introducing a liquid to the interior volume, at least one inlet for introducing a gas comprising oxygen and under pressure to the interior volume, at least one liquid product outlet for removing from the interior volume a product comprising a liquid or slurry of solid in a liquid, and at least one vent for removing a high pressure reaction overhead vapor from the interior volume; a separation device in fluid communication with the reaction vessel for receiving into the device a high pressure reaction overhead vapor removed from at least one vent in the reaction vessel and comprising at least column comprising at least one vapor inlet adapted to receive high pressure reaction overhead vapor for flow through the column, at least one liquid inlet adapted to receive reflux liquid for flow through the column countercurrent to the high pressure reaction overhead vapor flow, means within the column and positioned intermediate vapor and liquid inlets and providing surface for contacting gas and liquid phases within the column such that a high pressure reaction vapor phase comprising gaseous C1-8 monocarboxylic acid and water vapor received into the column is separated into a liquid phase rich in the C1-8 monocarboxylic acid but lean in water and a high pressure gaseous overhead stream comprising water and not more than about 10% of the C1-8 monocarboxylic acid in the high pressure reaction overhead vapor received into the column, at least one liquid outlet for removing a liquid therefrom, and at least one vent located above the liquid inlet for removal from the column of the high pressure gaseous overhead stream comprising water; at least one condensing means in fluid communication with the separation device for receiving a high pressure gaseous overhead stream comprising water comprising at least one gas inlet adapted to receive the high pressure gaseous overhead stream comprising water, at least one vent adapted for removal of a high pressure off-gas from the heat exchange means, heat transfer means for exchanging heat between a high pressure gaseous overhead stream introduced into the heat exchange means and a heat transfer medium and partially condense from the gas a liquid comprising water; and expansion means for extracting energy in the form of work comprising at least one gas inlet for receiving the high pressure off-gas from the condensing means and at least one gas outlet for expelling a vent gas stream at a pressure lower than inlet pressure.

As shown in FIG. 1, oxidation reaction vessel 4 comprises a substantially cylindrical shell that defines a substantially enclosed interior volume. In use, a lower portion of the interior volume contains a liquid reaction body while a reaction overhead vapor is contained in a portion of the interior volume above the liquid level. The interior volume is in communication with the exterior of the reaction vessel through a plurality of inlets through which liquid aromatic feed material, solvent and soluble forms of catalyst are introduced from liquid charge vessels (not shown) and compressed air or another source of oxygen gas is introduced from a compressor or other suitable device (not shown). The inlets preferably are disposed such that liquid and gaseous components are introduced below the liquid level in the interior of the vessel.

The reaction vessel 4 also includes at least one outlet for removing from the interior a liquid phase reaction mixture which includes a crude product comprising aromatic carboxylic acid and oxidation by-products, the same typically being present in solution in the liquid or as solid particles suspended or slurried in the liquid or both dissolved and suspended in the liquid. Reaction vessel 4 also comprises at least one vent or outlet for removal from the vessel interior of a high pressure reaction vapor phase evaporated from the liquid reaction body via line 111. Such vent preferably is positioned to correspond to an upper portion of the vessel when it is in position for process use.

A preferred reaction vessel design is a substantially cylindrical vessel having a central axis extending substantially vertically when the vessel is positioned for process use. The vessel is adapted for use with a stirring mechanism with shaft having one or more impellers mounted thereon and capable of being rotated within the interior of the reaction vessel to stir the liquid reaction mixture present in the vessel during process use. In preferred embodiments of the invention, at least two impellers or mixing features are mounted on the shaft for mixing of gaseous and liquid components within the liquid reaction body without adverse settling of solids in lower portions of the vessel. Axial flow impellers, generally configured as propellers, radial flow mixers, such as flat blade disc turbines and disperser discs, helical ribbon mixing elements, pitched blade turbines with blades pitches for upward or downward flow, anchor-type mixers providing predominantly tangential flow and other configurations are suited for mixing the liquid phase oxidation reaction system and preferably are used in various combinations to account for greater solids content in lower regions of the liquid reaction mixture, greater gas content in upper regions and other characteristics of the liquid phase reaction mixture that can vary throughout the liquid body. Other designs are disclosed in U.S. Pat. No. 5,198,156, describing mixing elements with radially extending, rotating blades mounted on a flat rotor and having a hollow blade configuration with a discontinuous leading edge, continuous trailing edge, absence of external concave surfaces and an open outer end and preferably used in conjunction with a vertical pipe or perforated gas sparger for gas distribution, and U.S. Pat. No. 5,904,423, which describes a mixer in which stirring elements are mounted at a downward angle on a central, rotating shaft and are wedge-shaped in the direction of movement through the liquid, with radial inner ends of the trailing edges of the blades angled outwardly in the direction of motion of the blades, and used with features for introducing a gas from below the stirring elements into a central cavity formed by a conical disk at an end of the shaft.

At least those portions of the reaction vessel, agitator shaft and mixing elements that contact the liquid reaction mixture and reaction overhead vapor in process use are constructed of substantially corrosion resistant materials. Examples include titanium metal and alloys and duplex stainless steels. Titanium metal is preferred.

In FIG. 1, reaction overhead vapor from reactor vessel 4 is directed via line 111 to a high efficiency distillation column 6 having high efficiency packing such as Koch FLEXIPAC, a type of structured packing available from KGGP LLC, and having at least 20, preferably at least 30, theoretical stages.

Preferably, the distillation column is a pressure rated column or tower, or a series of columns or towers, equipped with at least one inlet for receiving a high pressure reaction overhead vapor, at least one inlet for introduction of reflux liquid, at least one outlet for removing a high pressure gaseous overhead stream from the separation, and a fractionating zone comprising internal structure providing surface to promote mass transfer between countercurrently flowing gas and liquid phases sufficient to provide suitable theoretical equilibrium stages for separation of solvent monocarboxylic acid and water in the vapor phase is a preferred separation device. Preferably, the device is designed for introduction of an inlet gas into a lower portion of the column or tower and introduction of reflux liquid at one or more upper location relative to the gas inlet and with an intermediately positioned fractionating zone so that countercurrent flow therethrough results from upward passage of vapor phase and downward flow, under force of gravity, of liquid supplied as reflux and condensed from the ascending vapor phase. Additional features of such a tower or column can comprise one or more outlet or inlet ports for removal or addition of one or more gas or liquid streams, for example, removal of a liquid rich in monocarboxylic acid separated from the vapor phase.

The separation device can also be provided with a reboiler or other suitable means for supplemental heat input although such means are not normally needed when a high pressure reaction vapor phase from a liquid phase oxidation reaction vessel is introduced substantially directly to the device or otherwise without appreciable cooling because the oxidation reactor effectively serves as a reboiler by reason of the exothermic nature of the oxidation reaction. In preferred embodiments, direct association or close coupling of the oxidation reactor and separation device are effectuated by connection directly or by suitable pressure rated piping or other conduits between one or more vents in the oxidation reaction vessel and one or more gas inlets to a separation device, such that a reaction vapor phase under liquid phase reaction conditions is removed from the reaction vessel and introduced into the separation device at the same or substantially the same temperature and pressure as in the reaction zone.

Preferably, the separation device is capable of separating water and solvent monocarboxylic acid vapors in the high pressure reaction overhead vapor introduced to the device such that a liquid phase with at least about 60 to 85 parts by weight solvent monocarboxylic acid per hundred parts by weight of the liquid and a high pressure gas containing about 45 to 65 parts by weight water per hundred parts by weight of the gas are formed. To achieve such separation, the fractionating zone of the separation device is configured with a plurality of theoretical equilibrium stages such as can be provided by internal trays, structured packing or other structure providing surfaces within the interior of the device for mass transfer between gaseous and liquid phases present in the device. At least about 20 theoretical equilibrium stages are preferred for such separations. Separation efficiency increases with increasing theoretical equilibrium stages, other things being equal, so there is no theoretical upper limit to the number of equilibrium stages that may be included in the separation devices used according to the invention. However, for practical purposes, separation such that an outlet gas from the separation device contains 10 wt. % or less of the solvent monocarboxylic acid content of the inlet vapor phase to the device can be accomplished with at least about 20 theoretical equilibrium stages and degrees of separation beyond that provided by about 70 such stages make additional stages impractical or economically inefficient.

A preferred separation device with structured packing has at least about 3 beds or zones of packing, and more preferably about 4 to about 6 such beds, to provide adequate surface and theoretical equilibrium stages for separation. An example of a suitable packing material is Flexipac structured packing, which is available from KGGP LLC in the form of thin sheets of corrugated metal arranged in a crisscrossing relationship to create flow channels and such that their intersections create mixing points for liquid and vapor phases. For a preferred separation device with trays, trays in the form or sieve or bubble cap trays are preferred and preferably have separation efficiencies of about 40 to about 60%. The number of trays for a given number of theoretical equilibrium stages can be calculated by dividing the number of stages by efficiency of the trays.

In process use, gas and liquid phases introduced into the separation device and present therein are at elevated temperatures and include water, monocarboxylic acid and other corrosive components, for example, bromine compounds and their disassociation products such as hydrogen bromide that are present in an oxidation reaction overhead gas when the catalyst used for the oxidation includes a source of bromine. Therefore, in preferred embodiments of the invention, internal structure and other features of the separation device that contact gases and liquids during process operation are constructed of suitable metals to resist corrosion and other damage due to such contact. Titanium metal is a preferred material of construction for such surfaces, including trays, packings or other structure of the fractionating zone. Titanium surfaces of such structure may be subject to undesirable accumulation of solid deposits comprising iron oxides from impurities present in various process liquids circulated through the equipment. Processes for controlling accumulations of iron oxide deposits or content of soluble iron impurities in process liquids are described in commonly assigned U.S. Pat. No. 6,852,879 and US 2002/374719 which are incorporated herein by reference.

As shown in FIG. 1, the high efficiency distillation column 6 performs a high efficiency separation of the reaction overhead vapor. A liquid bottoms stream 121 resulting from the high efficiency separation and primarily comprising acetic acid solvent is returned to the reactor vessel 4.

The separation device of the apparatus according to this aspect of the invention is in flow communication with condensing means. The condensing means is adapted to receive a gas stream comprising high pressure gaseous overhead stream removed from the separation device and to partially condense from the high pressure gaseous overhead stream a liquid condensate comprising water substantially free of organic impurities, also leaving a high pressure condenser off-gas that comprises incondensable components of the gas introduced to the separation device and from about 40 wt % to about 80 wt % of water vapor present in the high pressure gaseous overhead stream. The condensing means also comprises at least one outlet for removing condensate liquid condensed from the gas introduced thereto and indirect heat exchange means for transferring heat between the inlet gas and a heat exchange fluid that is introduced to the device at a lower temperature or pressure and removed at a higher temperature or pressure. The condensing means optionally also includes means for directing condensate liquid to purification equipment, with such means preferably being in flow communication with at least one vessel or liquid receiving means in a purification process apparatus such that condensate liquid removed through an outlet for removal of condensate can be transferred directly to the purification equipment. The condensing means can comprise a single or series of heat exchange devices, such as shell and tube heat exchangers, plate and frame heat exchangers or other suitable heat exchange devices, in which heat from the inlet gas is transferred to a heat exchange medium such as water, steam or another heat transfer fluid, to increase the temperature or pressure of the heat exchange fluid. Use of multiple heat exchange devices in series can be advantageous for generating steam or other heat exchange fluids at different pressures or temperatures, and condensate liquid at different temperatures, for usages with different steam pressure and liquid temperature requirements or preferences.

The condenser is typically constructed of metals or alloys characterized by corrosion resistance suited to the nature of the high temperature gas streams and cooled liquids present circulated or present therein during process use. Stainless steel internal surfaces are preferred although other metals and alloys are also suitable.

Referring again to FIG. 1, a high pressure gaseous overhead stream 123 resulting from the high efficiency separation and primarily comprising water and also containing unreacted oxidant gas is directed to a condenser 8 where it is partially condensed such that water in the high pressure gaseous overhead stream 123, and preferably from about 30 wt % to about 50 wt % of the water in the high pressure gaseous overhead stream, is converted to liquid form and transferred via line 25 to the top of high efficiency distillation column 6 for use as reflux in the column. Energy is extracted during partial condensation by exchanging heat from the condenser 8 with suitable heat sink material such as water. High pressure off-gas 127 is directed from the condenser 8 to a preheater 10 where it is heated. The heated high pressure off-gas 129 is directed to an oxidative treatment unit 12 where organic components and by-products in the heated high pressure off-gas 129 are oxidized to compounds more suited for beneficial environmental management. The oxidized high pressure off-gas 131 is directed to an expander 14 which is connected to generator 16. Energy from the oxidized high pressure off-gas 131 is converted to work in the expander 14 and such work is converted to electrical energy 135 by generator 16. Vent gas 133 exiting the expander 14 is preferably treated prior to release into the atmosphere. Such treatment may include caustic scrubbing, to remove any remaining impurities, such as bromine, prior to atmospheric release. Such treatment can also include removing water which can be used elsewhere in the process, used in related processes, used in other processes or disposed of.

In existing energy recovery schemes, instead of partially condensing the high pressure gaseous overhead stream 123 using the condenser 8, the high pressure gaseous overhead stream 123 would have been completely condensed and energy would be extracted during complete condensation by exchanging heat from with suitable heat sink material. High pressure off-gas resulting from complete condensation would be comprised largely of nitrogen gas and other non-condensables and would have very little, if any, water. Such high pressure off-gas resulting from complete condensation may be subjected to further energy recovery using an expander. Such complete condensation scheme, however, results in significantly less energy recovery than the combination of heat energy recovery using partial condensation and recovery of energy in the form of work in accordance with this invention. Although partial condensation results in less energy recovery from the heat extraction process, the increase in energy recovery from work extraction is greater than the energy not recovered from the heat extraction process. The unexpected beneficial effect of this invention can be further demonstrated with reference to FIG. 2, which is a comparative example of energy recovery from liquid phase oxidation of aromatic hydrocarbons to produce aromatic carboxylic acids, and with reference to FIG. 3.

Figure 2:
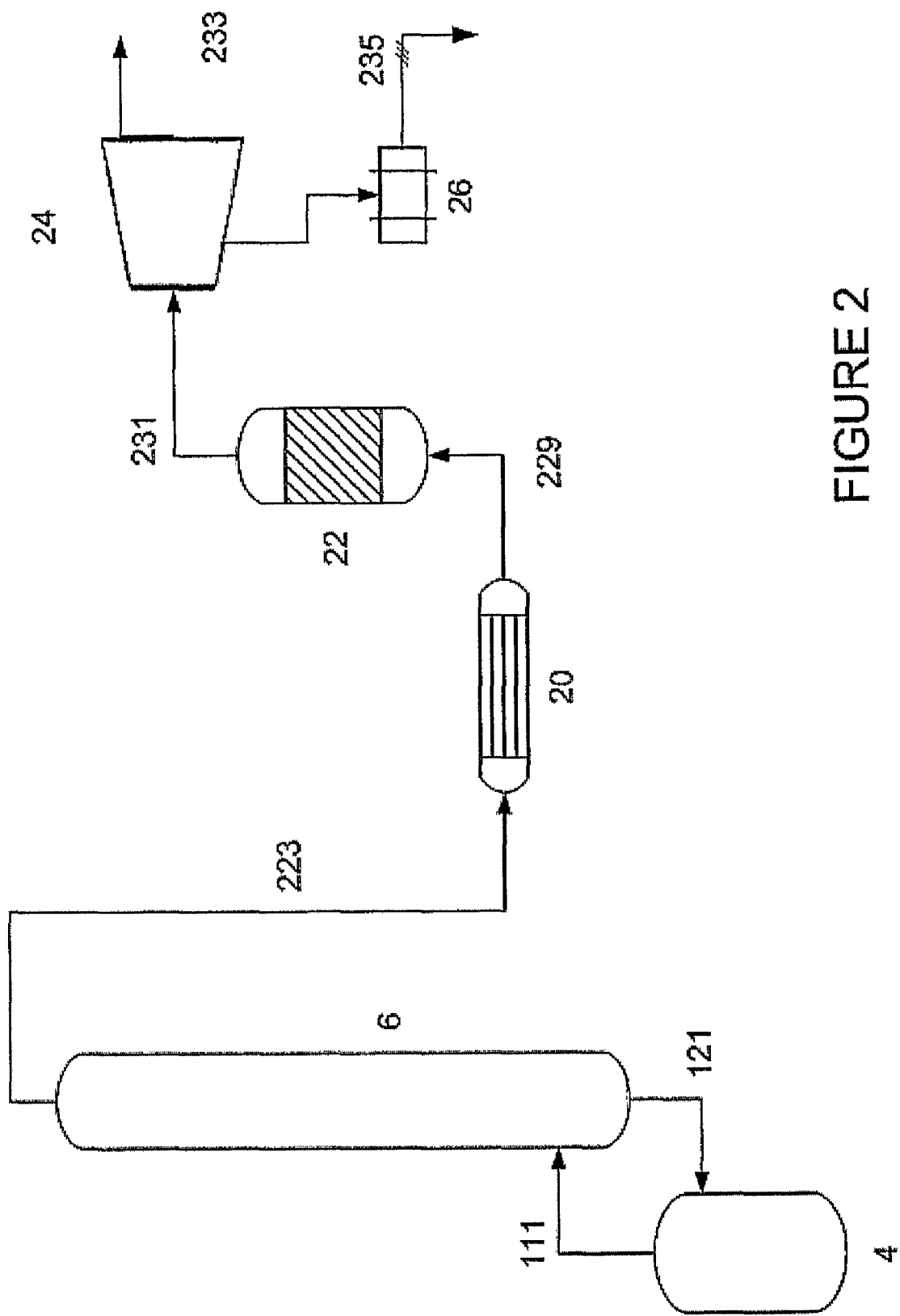
FIG. 2 represents an existing scheme for recovering energy in the liquid phase oxidation of aromatic hydrocarbons to produce aromatic carboxylic acids.

In FIG. 2, reactor overhead vapor 111 from reactor 4 is directed to a high efficiency distillation column 6 which performs a high efficiency separation of the reactor overhead vapor 111. A liquid bottoms stream 121 from the high efficiency distillation column 6 is returned to the reactor 4.

In FIG. 2, a high pressure gaseous overhead stream 223 is directed to a preheater 20 where it is heated in preparation for oxidation treatment for destruction of organic impurities in the off-gas. The heated high pressure stream 229 is directed to a treatment unit for catalytic oxidation 22 where organic components and byproducts in the heated high pressure stream 223 are oxidized to compounds more suited for beneficial environmental management. The oxidized high pressure stream 231 is directed to an expander 24 for energy recovery and energy depleted vent gas 233 exits the expander 24. Energy from the oxidized high pressure stream 231 is converted to work in the expander 24 and such work is converted to electrical energy 235 by generator 26.

FIG. 3 illustrates the surprisingly beneficial energy recovery achieved in an embodiment of this invention in comparison to comparable embodiments of certain other methods under similar process conditions. Examples A, B and C represent energy that would be recovered from a liquid phase oxidation process for converting aromatic hydrocarbons into aromatic carboxylic acids having a stoichiometry of 2 moles of oxygen consumed for each mole of aromatic hydrocarbon produced, wherein the reactor is operated at about 197° C. and about 16 kg/cm$^2$, and wherein acetic acid is used as a reaction solvent and the liquid phase is maintained at about 14 wt % water and wherein reactor overhead vapor comprises about 5 wt % oxygen. In such a process, high efficiency separation is performed upon the reactor overhead vapor such that over 98 wt % of the acetic acid present in the reactor overhead vapor is removed to form a high pressure gaseous overhead stream.

Bar A represents the energy recovered in such a process if energy was extracted as heat using complete condensation of the high pressure gaseous overhead stream and additional energy was extracted work by subjecting high pressure off-gas from such complete condensation (containing primarily nitrogen and other non-condensables) to further energy recovery in the form of work using an expander. The filled area of the bar represents energy recovered in the form of work from expansion and the clear area of the bar represents energy recovered in the form of heat using a condenser.

Bar B shows the energy recovered in a process using the same oxidation conditions and high efficiency separation as used for Bar A if energy recovery was conducted as shown in FIG. 2. The process of FIG. 2 does not involve heat energy recovery from condensation and relies solely on energy recovery in the form of work by directing the high pressure gaseous overhead stream to an expander. Bar C represents energy recovered, using the same oxidation conditions and high efficiency separation as used for Bar A, if energy recovery was conducted in accordance with an embodiment of this invention.

A comparison between bars A and B reveals less than 2% difference in energy recovered whether the process is conducted according to FIG. 2 or using an energy recovery scheme using complete condensation followed by expansion of non-condensable gases. Based on the energy recovered in prior art efforts to recover energy from oxidation reactor overhead vapor from the liquid-phase oxidation of aromatic hydrocarbons to form aromatic carboxylic acids, a process conducted in accordance with this invention would not have been expected to achieve any significant increase in recovered energy. However, as shown by bar C, we have surprisingly found that this invention can achieve greater than 16% increase in energy recovery in comparison to bar A. Even though less energy is recovered from the condenser as a result of partial condensation, the surprisingly greater increase in energy recovered from the expander results in greater overall energy recovery.

The significantly greater energy recovery realized by this invention allows more effective utilization of energy resources and significantly reduces the net energy consumption in making aromatic carboxylic acids from aromatic hydrocarbons. Furthermore, such significantly greater energy recovery significantly reduces the net energy needed to produce many chemical and polymer compounds which are derived from aromatic carboxylic acids.

That which is claimed is:

1. A process for energy recovery during the production of aromatic carboxylic acids by liquid phase oxidation of aromatic hydrocarbons wherein reaction overhead vapor comprising reaction solvent and water is formed, the process comprising the steps of:
    a) performing a high efficiency separation on the reaction overhead vapor to form at least a high pressure gaseous overhead stream comprising water and organic impurities;
    b) recovering heat energy from the high pressure gaseous overhead stream by exchanging heat with a heat sink material such that a condensate comprising from about 20 wt % to about 60 wt % of the water present in the high pressure gaseous overhead stream is formed and a high pressure off-gas comprising about 40 to about 80 wt % of the water present in the high pressure gaseous overhead stream remains uncondensed, and temperature or pressure of the heat sink material is increased;
    c) expanding high pressure off-gas remaining uncondensed from step (b) comprising about 40 to about 80 wt % of the water present in the high pressure gaseous overhead stream to recover energy in the form of work from the high pressure off-gas; and
    (d) directing heat sink material increased in temperature or pressure in step (b) to another step of the process for heating or to use outside the process.

2. The process of claim 1 further comprising the step of oxidizing at least a portion of the organic impurities by subjecting the high pressure off-gas to thermal oxidation before recovering energy in the form of work from the high pressure off-gas.

3. The process of claim 1 wherein the heat sink material comprises water such that heat exchange with the high pressure gaseous overhead stream in step (b) generates steam.

4. A process for the production of aromatic carboxylic acid, the process comprising the steps of:
    a) oxidizing, in a reaction zone comprising at least one reaction vessel, aromatic hydrocarbon with an oxidant gas to form aromatic carboxylic acid in a reaction solvent comprising a $C_1$-$C_8$ monocarboxylic acid in the presence of a catalyst comprising at least one heavy metal with atomic weight in the range of about 23 to about 178 and a halogen promoter under liquid phase conditions at temperatures in the range from about 120° C. to about 250° C. to form an aromatic carboxylic acid product and a reaction overhead vapor comprising water and solvent vapors;
    b) performing a high efficiency separation on at least a portion of the reaction overhead vapor to form a liquid bottoms stream comprising at least 95 wt % of the solvent from the reaction overhead vapor and a high pressure gaseous overhead stream comprising at least 50 wt % of the water from the removed portion of the reaction overhead vapor;

c) recovering energy in the form of heat by exchanging heat from the high pressure gaseous overhead stream with a heat sink material such that a condensate comprising from about 20 wt % to about 60 wt % of the water in the high pressure gaseous overhead stream is formed and a high pressure off-gas comprising about 40 to about 80 wt % of the water present in the high pressure gaseous overhead stream remains uncondensed, and temperature or pressure of the heat sink material is increased;

d) expanding high pressure off-gas remaining uncondensed from step (c) comprising about 40 to about 80 wt % of the water present in the high pressure gaseous overhead stream to recover energy in the form of work from the high pressure off-gas; and (e) directing heat sink material that is increased in temperature or pressure in step (c) to another step of the process for heating or to use outside the process.

5. The process of claim 4 further comprising the step of returning at least a portion of the liquid bottoms stream to the reaction zone.

6. The process of claim 4 wherein the heat sink material comprises water such that heat exchange with the high pressure gaseous overhead stream in step (c) generates steam.

7. The process of claim 4 wherein the $C_1$-$C_8$ monocarboxylic acid solvent is acetic acid.

8. The process of claim 4 wherein the at least one heavy metal comprises cobalt and one or more secondary metal selected from the group consisting of manganese, cerium, zirconium and hafnium.

9. The process of claim 8 wherein the at least one heavy metal is present in an amount ranging from about 100 ppmw to about 6000 ppmw.

10. The process of claim 8 wherein the halogen promoter is a bromine promoter.

11. The process of claim 10 wherein the bromine promoter comprises one or more bromine compounds selected from the group consisting of $Br_2$, HBr, NaBr, KBr, $NH_4Br$, benzylbromide, bromo acetic acid, dibromo acetic acid, tetrabromoethane, ethylene dibromide, bromoacetyl bromide, bromoanthracene, and dibromoanthracene.

12. The process of claim 10 wherein the heat sink material comprises water such that heat exchange with the high pressure gaseous overhead stream in step (b) generates steam.

13. The process of claim 4 wherein oxidation is conducted at a pressure in the range from about 5 to about 40 $kg/cm^2$ gauge.

14. The process of claim 13 wherein the aromatic carboxylic acid is terephthalic acid.

15. The process of claim 14 wherein the aromatic hydrocarbon comprises paraxylene.

16. The process of claim 3 wherein heat exchange with the high pressure gaseous overhead stream in step (b) is conducted in stages to generate steam at different pressures.

17. The process of claim 3 wherein steam generated by heat exchange in step (b) is directed to another part of the process for heating.

18. The process of claim 6 wherein heat exchange with the high pressure gaseous overhead stream in step (c) is conducted in stages to generate steam at different pressures.

19. The process of claim 1 wherein heat energy extracted in step (b) is used for heating in another part of the process.

20. The process of claim 4 wherein energy in the form of heat recovered in step (c) is used for heating in another part of the process.

* * * * *